US008569560B2

(12) United States Patent
Schrodi et al.

(10) Patent No.: US 8,569,560 B2
(45) Date of Patent: Oct. 29, 2013

(54) SYNTHESIS OF TERMINAL ALKENES FROM INTERNAL ALKENES VIA OLEFIN METATHESIS

(71) Applicant: Elevance Renewable Sciences, Inc., Woodridge, IL (US)

(72) Inventors: Yann Schrodi, Northridge, CA (US); Richard L. Pederson, San Gabriel, CA (US); Hiroki Kaido, Eden Praire, MN (US); Michael J. Tupy, Crystal, MN (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

(21) Appl. No.: 13/622,613

(22) Filed: Sep. 19, 2012

(65) Prior Publication Data
US 2013/0035532 A1 Feb. 7, 2013

Related U.S. Application Data

(62) Division of application No. 12/445,000, filed as application No. PCT/US2007/081427 on Oct. 15, 2007.

(60) Provisional application No. 60/851,693, filed on Oct. 13, 2006.

(51) Int. Cl.
C07C 1/00 (2006.01)
C07C 6/00 (2006.01)

(52) U.S. Cl.
USPC .......................................... 585/639; 585/643

(58) Field of Classification Search
USPC ................................................ 585/639, 643
See application file for complete search history.

(56) References Cited

U.S. PATENT DOCUMENTS

| | | |
|---|---|---|
| 5,142,072 A | 8/1992 | Stipp et al. |
| 5,312,940 A | 5/1994 | Grubbs et al. |
| 5,710,298 A | 1/1998 | Grubbs et al. |
| 5,728,785 A | 3/1998 | Grubbs et al. |
| 5,728,917 A | 3/1998 | Grubbs et al. |
| 5,750,815 A | 5/1998 | Grubbs et al. |
| 5,811,515 A | 9/1998 | Grubbs et al. |
| 5,831,108 A | 11/1998 | Grubbs et al. |
| 5,849,851 A | 12/1998 | Grubbs et al. |
| 5,880,231 A | 3/1999 | Grubbs et al. |
| 5,917,071 A | 6/1999 | Grubbs et al. |
| 5,922,863 A | 7/1999 | Grubbs et al. |
| 5,939,504 A | 8/1999 | Woodson, Jr. et al. |
| 5,969,170 A | 10/1999 | Grubbs et al. |
| 5,977,393 A | 11/1999 | Grubbs et al. |
| 6,020,443 A | 2/2000 | Woodson, Jr. et al. |
| 6,040,363 A | 3/2000 | Warner et al. |
| 6,080,826 A | 6/2000 | Grubbs et al. |
| 6,107,420 A | 8/2000 | Grubbs et al. |
| 6,169,198 B1 | 1/2001 | Fischer et al. |
| 6,197,894 B1 | 3/2001 | Sunaga et al. |
| 6,211,315 B1 | 4/2001 | Larock et al. |
| 6,215,019 B1 | 4/2001 | Pederson et al. |
| 6,284,852 B1 | 9/2001 | Lynn et al. |
| 6,306,988 B1 | 10/2001 | Grubbs et al. |
| 6,310,121 B1 | 10/2001 | Woodson, Jr. et al. |
| 6,316,380 B1 | 11/2001 | Nolan et al. |
| 6,323,296 B1 | 11/2001 | Warner et al. |
| 6,376,690 B1 | 4/2002 | Grubbs et al. |
| 6,409,875 B1 | 6/2002 | Giardello et al. |
| 6,410,110 B1 | 6/2002 | Warner et al. |
| 6,410,666 B1 | 6/2002 | Grubbs et al. |
| 6,426,419 B1 | 7/2002 | Grubbs et al. |
| 6,433,101 B1 | 8/2002 | Woodson, Jr. et al. |
| 6,465,590 B1 | 10/2002 | Maughon et al. |
| 6,486,264 B1 | 11/2002 | Tsunogae et al. |
| 6,525,125 B1 | 2/2003 | Giardello et al. |
| 6,583,236 B1 | 6/2003 | Giardello et al. |
| 6,610,626 B2 | 8/2003 | Grubbs et al. |
| 6,613,910 B2 | 9/2003 | Grubbs et al. |
| 6,620,955 B1 | 9/2003 | Pederson et al. |
| 6,696,597 B2 | 2/2004 | Pederson et al. |
| 6,759,537 B2 | 7/2004 | Grubbs et al. |
| 6,794,534 B2 | 9/2004 | Grubbs et al. |
| 6,803,429 B2 | 10/2004 | Morgan et al. |

(Continued)

FOREIGN PATENT DOCUMENTS

| | | |
|---|---|---|
| EP | 0429995 A2 | 6/1991 |
| EP | 1408064 A1 | 4/2004 |

(Continued)

OTHER PUBLICATIONS

Anderson et al., "Synthesis and Reactivity of Olefin Metathesis Catalysts Bearing Cyclic (Alkyl)(Amino) Carbenes," Angewandte Chemie International Edition, vol. 46, 2007, pp. 7262-7265.

(Continued)

Primary Examiner — Deborah D Carr
(74) Attorney, Agent, or Firm — Brinks Hofer Gilson & Lione

(57) ABSTRACT

This disclosure relates generally to olefin metathesis, and more particularly relates to the synthesis of terminal alkenes from internal alkenes using a cross-metathesis reaction catalyzed by an olefin metathesis catalyst. According to one aspect, for example, a method is provided for synthesizing a terminal olefin, the method comprising contacting, in the presence of a ruthenium alkylidene metathesis catalyst, an olefinic substrate comprised of at least one internal olefin with a cross metathesis partner comprised of an alpha olefinic reactant, under reaction conditions effective to allow cross-metathesis to occur, wherein the reaction conditions include a reaction temperature of at least 35° C. The methods, compositions, reactions and reaction systems herein disclosed have utility in the fields of catalysis, organic synthesis, and industrial chemistry.

26 Claims, No Drawings

(56) References Cited

U.S. PATENT DOCUMENTS

| | | | |
|---|---|---|---|
| 6,818,586 B2 | 11/2004 | Grubbs et al. | |
| 6,838,489 B2 | 1/2005 | Bell et al. | |
| 6,884,859 B2 | 4/2005 | Grubbs et al. | |
| 6,900,347 B2 * | 5/2005 | Paulson et al. | 560/261 |
| 6,921,735 B2 | 7/2005 | Hoveyda et al. | |
| 6,921,736 B1 | 7/2005 | Nolan et al. | |
| 6,946,533 B2 | 9/2005 | Grubbs et al. | |
| 6,962,729 B2 | 11/2005 | Tokas et al. | |
| 6,987,154 B2 | 1/2006 | Choi et al. | |
| 7,026,495 B1 | 4/2006 | Pederson et al. | |
| 7,034,096 B2 | 4/2006 | Choi et al. | |
| 7,109,348 B1 | 9/2006 | Nolan | |
| 7,119,216 B2 | 10/2006 | Newman et al. | |
| 7,176,336 B2 | 2/2007 | Maughon et al. | |
| 7,205,424 B2 | 4/2007 | Nolan | |
| 7,285,593 B1 | 10/2007 | Giardello et al. | |
| 7,314,904 B2 | 1/2008 | Nadolsky et al. | |
| 7,329,758 B1 | 2/2008 | Grubbs et al. | |
| 7,365,140 B2 | 4/2008 | Piers et al. | |
| 7,507,854 B2 | 3/2009 | Lee et al. | |
| 7,576,227 B2 | 8/2009 | Lysenko | |
| 7,585,990 B2 | 9/2009 | Toor et al. | |
| 7,598,330 B2 | 10/2009 | Grubbs et al. | |
| 7,622,590 B1 | 11/2009 | Nolan et al. | |
| 7,678,932 B2 | 3/2010 | Thurier et al. | |
| 7,812,185 B2 | 10/2010 | Burdett et al. | |
| 8,067,610 B2 * | 11/2011 | Schrodi | 548/103 |
| 2002/0095007 A1 | 7/2002 | Larock et al. | |
| 2003/0055262 A1 | 3/2003 | Grubbs et al. | |
| 2003/0100776 A1 | 5/2003 | Grubbs et al. | |
| 2003/0186035 A1 | 10/2003 | Cruce et al. | |
| 2005/0070750 A1 | 3/2005 | Newman et al. | |
| 2005/0261451 A1 | 11/2005 | Ung et al. | |
| 2006/0079704 A1 | 4/2006 | Lacombe et al. | |
| 2006/0289138 A1 | 12/2006 | Borsinger et al. | |
| 2007/0179307 A1 | 8/2007 | Olivier-Bourbigou et al. | |
| 2007/0270621 A1 | 11/2007 | Millis et al. | |
| 2008/0027194 A1 | 1/2008 | Schrodi | |
| 2008/0064891 A1 | 3/2008 | Lee | |
| 2009/0048459 A1 | 2/2009 | Tupy et al. | |
| 2009/0126602 A1 | 5/2009 | Murphy et al. | |
| 2009/0217568 A1 | 9/2009 | Murphy et al. | |
| 2009/0220443 A1 | 9/2009 | Braksmayer et al. | |
| 2009/0259065 A1 | 10/2009 | Abraham et al. | |
| 2009/0264672 A1 | 10/2009 | Abraham et al. | |
| 2010/0047499 A1 | 2/2010 | Braksmayer et al. | |
| 2010/0094034 A1 | 4/2010 | Kaido et al. | |

FOREIGN PATENT DOCUMENTS

| | | |
|---|---|---|
| EP | 1810960 A1 | 7/2007 |
| FR | 2878246 A1 | 5/2006 |
| JP | 56-077243 A | 6/1981 |
| JP | 09-014574 A | 1/1997 |
| SU | 1565872 A1 | 7/1988 |
| WO | WO 94/23836 A1 | 10/1994 |
| WO | WO 96/04289 A1 | 2/1996 |
| WO | WO 01/36368 A2 | 5/2001 |
| WO | WO 03/093215 A1 | 11/2003 |
| WO | WO 2004/062763 A2 | 7/2004 |
| WO | WO 2005/026106 A1 | 3/2005 |
| WO | WO 2005/080455 A1 | 9/2005 |
| WO | WO 2006/052688 A2 | 5/2006 |
| WO | WO 2007/081987 A2 | 7/2007 |
| WO | WO 2007/103398 A1 | 9/2007 |
| WO | WO 2007/103460 A2 | 9/2007 |
| WO | WO 2008/008420 A1 | 1/2008 |
| WO | WO 2008/010961 A2 | 1/2008 |
| WO | WO 2008/046106 A2 | 4/2008 |
| WO | WO 2008/048520 A2 | 4/2008 |
| WO | WO 2008/048522 A1 | 4/2008 |
| WO | WO 2008/063322 A2 | 5/2008 |
| WO | WO 2008/140468 A2 | 11/2008 |

OTHER PUBLICATIONS

Baumann et al., "Natural Fats and Oils—Renewable Raw Materials for the Chemical Industry," Angewandte Chemie International Edition in English, vol. 27, 1988, pp. 41-62.

Biermann et al., "New Syntheses with Oils and Fats as Renewable Raw Materials for the Chemical Industry,", Angewandte Chemie International Edition, vol. 39, 2000, pp. 2206-2224.

Boelhouwer et al., "Metathesis Reactions of Fatty Acid Esters," Progress of Lipid Research, Pergamon Press, vol. 24, No. 3, 1985, pp. 243-267.

Chatterjee et al., "Synthesis of Trisubstituted Alkenes via Olefin Cross-Metathesis," Organic Letters, vol. 1, No. 11, 1999, pp. 1751-1753.

Choi et al., "Olefin Metathesis Involving Ruthenium Enoic Carbene Complexes," Journal of the American Chemical Society, vol. 123, No. 42, 2001, pp. 10417-10418.

Connon et al., "A Solid-Supported Phosphine-Free Ruthenium Alkylidene for Olefin Metathesis in Methanol and Water," Bioorganic & Medical Chem Letters, vol. 12, No. 14, 2002, pp. 1873-1876.

Delaude et al., Metathesis, Kirk-Othmer Encyclopedia of Chemical Technology, Dec. 2005, vol. 26, pp. 920-958.

Dunne et al., "A Highly Efficient Olefin Metathesis Initiator: Improved Synthesis and Reactivity Studies," Tetrahedron Letters, vol. 44, No. 13, 2003, pp. 2733-2736.

Erhan et al. , "Drying Properties of Metathesized Soybean Oil," Journal of American Oil Chemists' Society, AOCS Press, vol. 74, No. 6, 1997, pp. 703-706.

Lavallo, "Stable Cyclic (Alkyl)(Amino) Carbenes as Rigid or Flexible, Bulky, Electron-Rich Ligands for Transition-Metal Catalysts: A Quaternary Carbon Atom Makes the Difference," Angewandte Chemie Int. Ed., vol. 44, 2005, pp. 5705-5709.

Maynard et al., "Purification Technique for the Removal of Ruthenium from Olefin Metathesis Reaction Products," Tetrahedron Letters, vol. 40, No. 22, 1999, pp. 4137-4140.

Mol, "Applications of Olefin Metathesis in Oleochemistry: An Example of Green Chemistry," Green Chemistry, Royal Society of Chemistry, Cambridge, GB, vol. 4, 2002, pp. 5-13.

Mol et al., "Metathesis in Oleochemistry," J Braz Chem Soc, vol. 9, No. 1, 1998, pp. 1-11.

Mol, "Catalytic Metathesis of Unsaturated Fatty Acid Esters and Oils," Topics in Catalysis, vol. 27, No. 1-4, 2004, pp. 97-104.

Ngo et al., Methathesis of Unsaturated Fatty Acids: Synthesis of Long-Chain Unsaturated[alpha],[omega]-Dicarboxylic Acids, Journal of the American Oil Chemists, Jul. 2006, vol. 83m Iss, 7, 8 pages.

Patel et al., "High conversion and productive catalyst turnovers in cross-metathesis reactions of natural oils with 2-butene", Green Chemistry, 2006, vol. 8, pp. 450-454.

Refvik et al., "Ruthenium-Catalyzed Metathesis of Vegetable Oils," Journal of American Oil Chemists' Society, JAOCS Press, vol. 76, No. 1, 1999, pp. 93-98.

Refvik, M.D. et al., "The Chemistry of Metatesized Soybean Oil," JAOCS, vol. 76, No. 1, 1999, pp. 99-102.

Schneider et al., "Synthesis of Highly Substituted Cyclopentane and Tetrahydrofuran Derivatives by Crossed Olefin Metathesis," Angewandte Chemi International Edition, vol. 35, No. 4, 1996, pp. 411-412.

Tian et al., "Model Studies and the ADMET Polymerization of Soybean Oil," Journal of American Oil Chemists' Society, AOCS Press, vol. 79, No. 5, 2002, pp. 479-488.

* cited by examiner

SYNTHESIS OF TERMINAL ALKENES FROM INTERNAL ALKENES VIA OLEFIN METATHESIS

STATEMENT OF JOINT RESEARCH AGREEMENT

This application was the subject of a Joint Research Agreement between Materia, Inc. and Cargill, Inc.

TECHNICAL FIELD

This disclosure relates generally to olefin metathesis, and more particularly relates to the synthesis of terminal alkenes from internal alkenes using a cross-metathesis reaction catalyzed by a selected olefin metathesis catalyst. The applications illustrated in this disclosure have utility in the fields of catalysis, organic synthesis, and industrial chemistry.

BACKGROUND

Ethenolysis is a specific cross metathesis reaction between an internal olefin and ethylene to produce terminal olefins. Scheme 1 demonstrates the ethenolysis reaction:

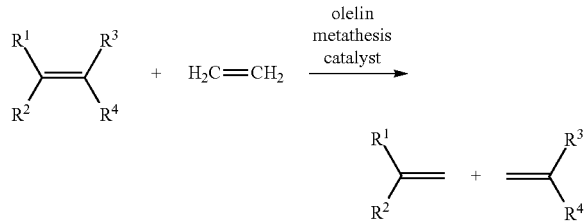

SCHEME 1

Examples of ethenolysis include the conversion of a mixture of ethylene and 2-butene into propene (as in the Phillips triolefin process and the Meta-4 process developed by the Institut Français du Pétrole), and the conversion of a mixture of ethylene and 2,4,4trimethyl-2-pentene into neohexane. These processes typically use heterogeneous, ill-defined olefin metathesis catalysts based oil tungsten and rhenium oxides and which are not compatible with air, water, oxygenates, and many functional groups. The ethenolysis reaction has also been implemented in the conversion of seed oil-derived substrates such as fatty acid methyl, esters (FAME) into terminally unsaturated carboxylic acids (e.g., 9-decenoic acid) and terminal olefins (e.g., 1-decene). The ethenolysis of FAME was originally performed with a heterogeneous, ill-defined rhenium catalyst to give turnover numbers (TON) of about 100. More recently, the ruthenium alkylidene catalyst $Cl_2(PCy_3)_2Ru=CH-CH=CPh_2$ was used for the ethenolysis of methyl oleate (MO). Several groups have used the so-called "first generation" Grubbs catalyst $Cl_2(PCy_3)_2Ru=CHPh$ ("C823") or the first generation Grubbs-Hoveyda catalyst ("C601") to promote the ethenolysis of vegetable oil-derived materials. Additionally, first generation Grubbs-like complexes that contain bicyclic phosphines were used in the ethenolysis of methyl oleate, although the highest ethenolysis turnover number reported to date for this reaction is 15,400. The cross metathesis of 1-butene and 11-eicosenyl acetate is reported, but this reaction is described to occur at 0° C. and high catalyst loading (e.g., 5 mol % catalyst loading; see example 9 in U.S. Pat. No. 6,900,347).

Accordingly, there is a need in the art for a more efficient method to produce terminal olefins from internal olefins.

It is therefore desirable to provide a convenient and effective route for the production of terminal olefins. Compared with known metathesis methods, an ideal process would: substantially reduce the amount of catalyst that is needed for the cross-metathesis reaction; allow the use of a mixture of internal olefins from a variety of sources; and allow the use of a variety of alpha-olefin cross metathesis partners. Unlike the process described in U.S. Pat. No. 6,900,347, which required significant cooling of the reaction mixture, an ideal process would allow for flexibility of reaction conditions.

SUMMARY OF THE DISCLOSURE

Accordingly, the disclosure is directed to addressing one or more of the aforementioned issues, and, provides method compositions and reactions systems for synthesizing a terminal olefin which can be performed according to any of the following aspects or any combinations thereof.

According to a first aspect, the method comprises contacting, in the presence of a ruthenium alkylidene metathesis catalyst, an olefinic substrate with a cross metathesis partner under reaction conditions effective to allow cross-metathesis to occur. The olefinic substrate comprises at least one internal olefin, and the cross metathesis partner comprises an alpha olefinic reactant. The reaction conditions include a reaction temperature of at least 35° C.

According to a second aspect, there is provided a method for synthesizing a terminal olefin. The method comprises contacting, under an inert atmosphere and in the presence of a ruthenium alkylidene metathesis catalyst, an olefinic substrate with a cross metathesis partner, under reaction conditions effective to allow cross-metathesis to occur. The olefinic substrate comprises at least one internal olefin, and the cross metathesis partner comprises an alpha olefinic reactant. The catalyst is present in an amount ranging from about 1 ppm (i.e., 0.0001 mol %) to about 50 ppm (i.e. 0.005 mol %) relative to the number of olefinic substrate double bonds.

According to a third aspect, there is provided a method for synthesizing a terminal olefin. The method comprises contacting, in an oxygen-containing atmosphere and in the presence of a ruthenium alkylidene metathesis catalyst, an olefinic substrate with a cross metathesis partner, under reaction conditions effective to allow cross-metathesis to occur. The olefinic substrate comprises at least one internal olefin, and the cross metathesis partner comprises an alpha olefinic reactant. The catalyst is present in an amount ranging from about 50 ppm (i.e., 0.005 mol %) to about 100 ppm (i.e., 0.01 mol %) relative to the number of olefinic substrate double bonds.

According to a fourth aspect, there is provided a method for synthesizing a terminal olefin. The method comprises contacting, under art inert atmosphere and in the presence of a ruthenium alkylidene metathesis catalyst, an olefinic substrate with a cross metathesis partner, under reaction conditions effective to allow cross-metathesis to occur. The olefinic substrate comprises a mixture of monoglycerides, diglycerides, and triglycerides, and the cross metathesis partner comprises an alpha-olefinic reactant.

According to a fifth aspect, there is provided a method for synthesizing a terminal olefin in a cross metathesis react ion of an olefinic substrate and a cross metathesis partner. The method comprises selecting at least one hydrophobic internal olefin as the olefinic substrate, and selecting as the cross metathesis partner an alpha olefin having a solubility of at least 0.25 M in the olefinic substrate when each of the olefinic substrate and the alpha olefin are in liquid form. The method further comprises contacting the olefinic substrate with the cross metathesis partner in the presence of a ruthenium alkylidene metathesis catalyst under reaction conditions effective to allow cross-metathesis to occur.

According to a sixth aspect, there is provided a method for synthesizing a terminal olefin. The method comprises contacting, under an inert atmosphere and in the presence of a ruthenium alkylidene metathesis catalyst, an olefinic substrate with a cross metathesis partner under reaction conditions effective to allow cross-metathesis to occur. The olefinic substrate comprises at least one internal olefin and the cross metathesis partner comprises an alpha olefinic reactant. The moles of the olefinic substrate, is approximately equal to 1 to 9 times the moles of the cross-metathesis partner.

According to a seventh aspect, there is provided a method for synthesizing a terminal olefin. The method comprises contacting, in the presence of a ruthenium alkylidene metathesis catalyst, an olefinic substrate with a cross metathesis partner, under reaction conditions effective to ensure that the olefinic substrate and the cross-metathesis partner are mostly in liquid form and to allow cross-metathesis to occur. The olefinic substrate comprises at least one internal olefin, and the cross metathesis partner comprises an alpha olefinic reactant.

According to an eight aspect, there is provided a method for synthesizing a terminal olefin. The method comprises contacting, in the presence of a ruthenium alkylidene metathesis catalyst, an olefinic substrate with a cross metathesis partner, under reaction conditions effective to allow cross-metathesis to occur, wherein the catalyst is a Grubbs-Hoveyda-type catalyst. The olefinic substrate comprises at least one internal olefin, and the cross metathesis partner comprises an alpha olefinic reactant.

According to a ninth aspect, there is provided a method for synthesizing a terminal olefin. The method comprises contacting, in the presence of a ruthenium alkylidene metathesis catalyst, an olefinic substrate with a cross metathesis partner, under reaction conditions effective to allow cross-metathesis to occur. The olefinic substrate comprises at least one internal olefin, and the cross metathesis partner comprises an alpha olefinic reactant wherein the olefinic substrate comprises at least one internal olefin having a molecular weight of at least: 250 g/mol, and/or is at least 15 carbon atoms According to a tenth aspect, there is provided a method for synthesizing a terminal olefin. The method comprises contacting, in the presence of a ruthenium alkylidene metathesis catalyst, an olefinic substrate with a cross metathesis partner under a pressure equal to or greater than 1.1 atm, and under reaction conditions effective to allow cross-metathesis to occur. The olefinic substrate comprises at least one internal olefin, and the cross metathesis partner comprises an alpha olefinic reactant.

DESCRIPTION OF THE PREFERRED EMBODIMENTS

Terminology and Definition:

Unless otherwise indicated, the disclosure is not limited to specific reactants, substituents, catalysts, reaction conditions, or the like, as such may vary, it is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "an α-olefin" includes a single α-olefin as well as a combination or mixture of two or more α-olefins, reference to "a substituent" encompasses a single substituent as well as two or more substituents, and the like.

As used in the specification and the appended claims, the terms "for example," "for instance," "such as," or "including" are meant to introduce examples that farther clarify more general subject matter. Unless otherwise specified, these examples are provided only as an aid for understanding the applications illustrated in the present disclosure, and are not meant to be limiting in any fashion.

In this specification and in she claims that fallow, reference will be made to a number of terms, which shall, be defined to have the following meanings:

The term "alpha-olefin" as used herein refers to organic compounds which are terminal olefins or alkenes with a chemical formula RR'C=$CH_2$, where R and R' are each independently alkyl, aryl, heteroalkyl, heteroaryl, alkoxy, alkylene, alkenyl, alkenylene, alkynyl alkynylene, aryloxy alkaryl, or acyl and R and R" are not both B.

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If sot otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, h-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkynylene" as used herein refers to a difunctional alkynyl group, where "alkynyl" is as defined above.

The terra "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 3 to 1.4 carbon atoms. Exemplary aryl groups contain one aromatic ring or two fused or linked aromatic rings, e.g., phenyl, naphthyl, biphenyl, diphenylether, diphenylamine, benzophenone, and the like, "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in farther detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctyl-naphthyl, 3-ethylcyclopenta-1,4-diene, and the like. Examples of aralkyl groups include, without limitation, benzyl, 2-phenyl-ethyl 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or
—(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" are used in the conventional sense to refer to a chloro, bromo, fluoro or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the terra "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and heterohydrocarbylene" refer to hydrocarbylene in which at least one carbon atom is replaced with a heteroatom. Unless otherwise indicated, the term "hydrocarbyl" and "hydrocarbylene" are to fee interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more-carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic." refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl," Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidine, morpholino, piperazino, piperidino, etc.

The term "heterocyclic carbene" refers to a neutral electron donor ligand comprising a carbene molecule, where the carbonic carbon atom is contained within a cyclic structure and where the cyclic structure also contains at least one heteroatom. Examples of heterocylic carbenes include "N-heterocyclic carbenes" wherein the heteroatom is nitrogen and "P-heterocyclic carbenes" wherein the heteroatom is phosphorus.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—CO-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)-substituted thiocarbamoyl (—CO—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—NH$_2$), cyano(—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl $C_6$-$C_{24}$ alkaryl. $C_6$-$C_{24}$ aralkyl, etc.), arylimino (—CR=N(aryl), where R=hydrogen, $C_1$-$C_{20}$alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)—aryl), $C_1$-$C_{24}$ alkylsulfonyl (—SO$_2$-alkyl), $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$)), phospho (—PO$_2$), phosphino (—PH$_2$), silyl (—SiR$_3$ wherein R is hydrogen or hydrocarbyl), and silyloxy (—O-silyl); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be farther substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In the molecular structures herein, the use of bold and dashed lines to denote particular conformation of groups follows the IUPAC convention. A bond indicated by a broken Sine indicates that the group in question is below the general plane of the molecule as drawn, and a bond indicated by a bold line indicates that the group at the position in question is above the general plane of the molecule as drawn.

Methods Compositions and Reaction Systems:

Accordingly, herein is described an olefin cross-metathesis method for synthesizing a terminal olefin from an olefinic substrate comprised of at least one internal olefin and a cross metathesis partner comprised of an alpha olefinic reactant. The reaction is carried out catalytically, in the presence of a ruthenium alkylidene metathesis catalyst.

The olefinic substrate comprises at least one internal olefin, and may have 2 or more internal olefins. For example, the olefinic substrate may comprise in the range of 2 to about 15, 2 to about 10, or 2 to about 5 internal olefins. By "internal olefin" is meant an olefin wherein each of the olefinic carbons is substituted by at least one non-hydrogen substituent. The non-hydrogen substituents are selected from hydrocarbyl, substituted hydrocarbyl, heteroatom-containing hydrocarbyl, substituted heteroatom-containing hydrocarbyl, and functional groups. The internal olefin is therefore at least disubstituted, and may further include additional non-hydrogen substituents such that the internal olefin is tri- or tetra-substituted. Each of the substituents on the internal olefinic carbons may be further substituted as described supra. The internal olefin may be in the Z- or B-configuration. When the olefinic substrate comprises a plurality of internal olefins, the olefinic substrate may comprise a mixture of internal olefins (varying in stereochemistry and/or substituent identity), or may comprise a plurality of internal olefins.

The olefinic substrate may be a single compound or a mixture of compounds. The olefinic substrate may be hydrophobic or hydrophilic, although in a preferred embodiment, the olefinic substrate is hydrophobic.

For example, the olefinic substrate may be represented by the formula $(R^I)(R^{II})C=C(R^{III})(R^{IV})$, wherein $R^I$, $R^{II}$, $R^{III}$, and $R^{IV}$ are independently selected from H, hydrocarbyl, substituted hydrocarbyl, heteroatom-containing hydrocarbyl, substituted heteroatom-containing hydrocarbyl, and functional groups, provided that at least one of $R^I$ and $R^{II}$ and at least one of $R^{III}$ and $R^{IV}$ is other than H. In a preferred embodiment, either $R^I$ or $R^{II}$ and either $R^{III}$ or $R^{IV}$ H, such that the internal olefin is di-substituted.

As another example, the olefinic substrate is an ester of glycerol (a "glyceride"), and has the structure of formula (I)

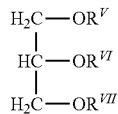

(I)

wherein $R^V$, $R^{VI}$, and $R^{VII}$ are independently selected from hydrogen, hydrocarbyl, substituted hydrocarbyl, heteroatom-containing hydrocarbyl, substituted heteroatom-containing hydrocarbyl, and functional groups, provided that at least one of $R^V$, $R^{VI}$, and $R^{VII}$ is other than hydrogen and comprises an internal olefin. In a preferred embodiment, the olefinic substrate comprises glycerol esterified with 1, 2, or 3 fatty acids, such that the olefinic substrate is a monoacylglycerol, diacylglycerol, or triacylglycerol (i.e., a monoglyceride, diglyceride, or triglyceride, respectively), or a mixture thereof. Each fatty acid-derived fragment of the olefinic substrate may independently be saturated, monounsaturated, or polyunsaturated, and may furthermore derive (or be derivable) front naturally-occurring fatty acids or from synthetic fatty acids. For example, the olefinic substrate may comprise glycerol esterified with one, two, or three fatty acids that are independently selected from $CH_3(CH_2)_n COOH$, where n is 2, 3, 4, 5, 6, 7, 8, 9, 10, 11, 12, 13, 14, 15, 16, 17, 18, 19, 20, 21, or 22, palmitoleic acid, vaccenic acid, erucic acid, oleic acid, alpha-linolenic acid, gamma-linolenic acid, linoleic acid, gadoleic acid, arachidonic acid, docosahexaenoic acid (i.e., DHA), eicosapentaenoic acid (i.e., EPA), and $CH_3-R^{VIII}-COOH$, where $R^{VIII}$ is substituted or unsubstituted $C_2$-$C_{24}$ alkenylene. The olefinic substrate may be solid (e.g., a fat) or liquid (e.g., an oil).

Preferred glycerides that may be used as the olefinic substrate are seed oils, or are compounds that derive from seed oils. Preferred seed oil sources include soybean oil, sunflower oil, canola oil, safflower oil, cottonseed oil, castor oil, rapeseed oil, peanut oil, corn oil, olive oil, palm oil, sesame oil, and grape seed oil.

The olefinic substrate may be a compound or mixture of compounds that is derived from a glyceride using any one or combination of methods well known in the chemical arts. Such methods include saponification, esterification, hydrogenation, isomerization, oxidation, and reduction. For example, the olefinic substrate may the carboxylic acid or mixture of carboxylic adds that result from the saponification of a monoacylglycerol, diacylglycerol, triacylglycerol, or mixture thereof. In a preferred embodiment, fee olefinic substrate is a fatty acid methyl, ester (FAME), i.e., the methyl ester of a carboxylic acid feat is derived from a glyceride. Sunflower FAME, safflower FAME, soy FAME (i.e., methyl soyate), and canola FAME are examples of such olefinic substrates. In addition, in some embodiments fee olefinic substrates include seed oil-derived compounds such as methyl oleate.

The cross-metathesis partner feat is reacted with fee at least one internal olefin may be any olefinic compound that is capable of undergoing a metathesis reaction with the olefinic substrate to generate a terminal alkene product. The cross-metathesis partner composes an alpha-olefin, wherein one olefinic carbon is unsubstituted and the other olefinic carbon is substituted with one or two non-hydrogen substituents. The substituted olefinic carbon may therefore be mono-substituted or di-substituted. The cross-metathesis partner may comprise a plurality of alpha olefins. A mixture of alpha-olefins may be used.

The cross-metathesis partner may comprise substituents selected from any of the substituents listed herein above. For example, the cross-metathesis partner may be an alpha-olefin that comprises a substituent comprising 1 to about 20 carbon atoms, about 10 carbon atoms, about 6 carton atoms, or about 3 carbon atoms.

As an example, the cross-metathesis partner may have the structure $H_2C=C(R^{IX})(R^X)$, wherein $R^{IX}$ and $R^X$ are independently selected from hydrogen, hydrocarbyl, substituted hydrocarbyl, heteroatom-containing hydrocarbyl, substituted heteroatom-containing hydrocarbyl and functional groups, provided that at least one of $R^{IX}$ and $R^X$ is a non-hydrogen substituent. Furthermore, $R^{IX}$ and $R^X$ may be linked to form a cycle. In a preferred embodiment, $R^{IX}$ and $R^X$ are independently selected from substituted or unsubstituted $C_1$-$C_{20}$ alkyl, substituted or unsubstituted $C_2$-$C_{20}$ alkenyl, substituted or unsubstituted $C_1$-$C_{20}$ alkynyl, substituted or unsubstituted heteroatom-containing $C_1$-$C_{20}$ alkyl, substituted or unsubstituted heteroatom-containing $C_2$-$C_{20}$ alkenyl, substituted or unsubstituted heteroatom containing $C_2$-$C_{20}$ alkynyl, substituted or unsubstituted $C_5$-$C_{24}$ aryl, substituted or unsubstituted $C_5$-$C_{24}$ alkaryl or substituted or unsubstituted $C_5$-$C_{24}$ aralkyl, substituted or unsubstituted heteroatom-containing $C_5$-$C_{24}$ aryl, substituted or unsubstituted heteroatom-containing $C_5$-$C_{24}$ alkaryl, substituted or unsubstituted heteroatom-containing $C_5$-$C_{24}$ aralkyl, and functional groups, with the proviso that when $R^{IX}$ equals $R^X$ $R^{IX}$ and $R^X$ are not equal hydrogen.

Examples of monosubstituted alpha-olefins that may be used for the cross-metathesis partner include 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene and larger alpha olefins, 2-propenol, 3-butenol, 4-pentenol, 5-hexenol, 6-heptenol, 7-octenol, 8-nonenol, 9-decenol, 10-undecenol, 11-dodecenol, 12-tridecenal, 13-tetradecenol, 14-pentadecenol 15-hexadecenoyl 16-heptadecenal, 17-octadecenol, 18-nonadecenal, 19-eiconsenol and larger alpha alkenols, 2-propenyl acetate, 3-butenyl acetate, 4-pentenyl acetate, 5-hexenyl acetate, 6-heptenyl acetate, 7-octenyl acetate, 8-nonenyl acetate, 9-decenyl acetate, 10-undecenyl acetate, 11-dodecenyl acetate, 12-tridecenyl acetate 13-tetradecenyl acetate, 14-pentadecenyl acetate, 15-hexadecenyl acetate, 16-heptadecenyl acetate, 17-octadecenyl acetate, 18-nonadecenyl acetate, 19-eicosenyl acetate and larger alpha-alkenyl acetates, 2-propenyl chloride, 3-butenyl chloride, 4-pentenyl chloride, 5-hexenyl chloride, 6-heptenyl chloride, 7-octenyl chloride, 8-nonenyl chloride, 9-decenyl chloride, 10-undecenyl chloride, 11-dodecenyl chloride, 12-tridecenyl chloride, 13-tetradecenyl chloride, 14-pentadecenyl chloride, 15-hexadecenyl chloride, 16-heptadecenyl chloride, 17-octadecenyl chloride, 18-nonadecenyl chloride, 19-eicosenyl chloride and larger alpha-alkenyl chlorides, bromides, and iodides, allyl cyclohexane, allyl cyclopentane, and the like.

Examples of disubstituted alpha-olefins that may be used for the cross-metathesis partner include isobutylene, 2-methylbut-1-ene, 2-methylpent-1-ene, 2-methylhex-1-ene, 2-methylhept-1-ene, 2-methyloct-1-ene, and the like.

Any combination of any of the above mentioned alpha olefin and cross metathesis partners can be reacted according to the disclosed methods, compositions and reaction systems. In an exemplary embodiment, a composition comprising 9-decenoic acid (9DA) and 9-undecenoic acid (9-UDA) can be prepared by the cross-metathesis of 1-propene with an internal olefin comprising a fatty acid, fatty ester, or mixture thereof. The interna olefin has a carbon-carbon double bond located at the C9-C10 position is the main chain of the fatty acid or fatty ester. As an example, the internal olefin may have the structure;

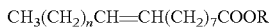

where n is an integer (typically 7); and
R is hydrogen (fatty acid) or a hydrocarbyl group (fatty ester).

Representative examples of suitable internal olefins include oleic acid, methyl oleate, and mixtures thereof. When a fatty ester is used as the internal olefin, the resulting cross-metathesis products are hydrolyzed according to known techniques in order to convert the ester functional groups into carboxylic acid groups. As is dictated by stoichiometry of the cross-metathesis reaction, the product composition typically comprises about 50 mole % 9-DA and about 50 mole % 9-UDA.

The reactions described herein include as reactants an olefinic substrate and a cross-metathesis partner. Individually, any of the reactants may be solid, liquid, or gaseous, although in a preferred embodiment, the reaction can be carried out under conditions to ensure that the olefinic substrate and the cross-metathesis partner are liquid. The use of a liquid cross-metathesis partner instead of a gaseous cross-metathesis partner such as ethylene is advantageous as it allows a convenient controlling of reaction pressures. In addition, in those embodiments, the demand on vapor condensers and vapor reclaiming equipment is reduced or eliminated It will be appreciated by those of skill in the art that the use of alpha-olefin cross-metathesis partners containing, for example, long alkyl substituents enables liquid-phase, room temperature (or greater) reactions and/or the use of reactors working at near atmospheric or slightly higher pressures.

In some preferred embodiments, the cross-metathesis partner is soluble in the olefinic substrate. The cross-metathesis partner may have a solubility of at least 0.25 M, at least 1 M, at least 3 M, or at least 5 M in the olefinic substrate. The cross-metathesis partner and the olefinic substrate may also be miscible at all concentrations.

As another example, the cross-metathesis partner has a low solubility in the olefinic substrate, and the cross-metathesis reaction occurs as an interfacial reaction. It should be noted that, when one or snore of the reactants is solid or gaseous, the reactions may still be canned out in the liquid phase by dissolving any solid or gaseous reactants in the liquid reactants, or by employing a solvent, as described infra.

The cross-metathesis partner may be provided in the form of a gas. Typically, the pressure of a gaseous cross-metathesis partner over the reaction solution is maintained in a range that has a minimum of about 10 psig, 15 psig, 50 psig, or 80 psig, and a maximum of about 250 psig, 200 psig, 150 psig, or 130 psig. Embodiments wherein the reaction pressures am lowered till near atmospheric pressure, and in particular till pressures slightly above atmospheric allow for a reduction in equipment costs compared to embodiments performed at high pressure (e.g. pressures greater than 350 psi).

The reactions of the disclosure are catalyzed by any of the metathesis catalysts that are described infra. The catalyst is typically added to the reaction medium as a solid, but may also be added as a solution wherein the catalyst is dissolved in an appropriate, solvent. It will be appreciated that the amount of catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction, in general, however, the catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, or 1000 ppm relative to the amount of the olefinic substrate. Catalyst loading, when measured in ppm relative to the amount of the olefinic substrate, is calculated using the equation $$ppm \text{ catalyst} = \frac{\text{moles catalyst}}{\text{moles olefinic substrate double bonds}} * 1{,}000{,}000$$

Alternatively, the amount of catalyst can be measured in terms of mol % relative to the amount of olefinic substrate, using the equation $$\text{mol \% catalyst} = \frac{\text{moles catalyst}}{\text{moles olefinic substrate double bonds}} * 100.$$

Thus, the catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, or 0.1 mol % relative to the olefinic substrate.

In a preferred embodiment, the reactions of the disclosure are carried out under a dry, inert atmosphere. Such an atmosphere may be created using any inert gas, including such gases as nitrogen and argon. The use of an inert atmosphere is optimal in terms of promoting catalyst activity, and reactions performed under an inert atmosphere typically are performed with relatively low catalyst loading. The reactions of the disclosure may also be carried out in an oxygen-containing and/or a water-containing atmosphere, and in one embodiment, the reactions are carried out under ambient conditions. The presence of oxygen, water, or other impurities in the reaction may, however, necessitate the use of higher catalyst loadings as compared with reactions performed under an inert atmosphere.

The olefin metathesis catalyst for carrying out the cross-metathesis reactions of the disclosure is preferably a Group 8 transition metal complex having the structure of formula (II)

in which the various substituents are as follows.

M is a Group 8 transition metal;
$L^1$, $L^2$ and $L^3$ are neutral electron donor ligands;
n is 0 or 1, such that $L^3$ may or may not be present;
m is 0, 1, or 2;
$X^1$ and $X^2$ are anionic ligands; and
$R^1$ and $R^2$ are independently selected from hydrogen, hydrocarbyl substituted hydrocarbyl, heteroatom-containing hydrocarbyl, substituted heteroatom-containing hydrocarbyl, and functional groups, wherein any two or more of $X^1$, $X^2$, $L^1$, $L^2$, $L^3$, $R^1$, and $R^2$ can be taken together to form a cyclic group, and further wherein any one or more of $X^1$, $X^2$, $L^1$, $L^2$, $L^3$, $R^1$, and $R^2$ may be attached to a support.

Preferred catalysts contain Ru or Os as the Group 8 transition metal, with Ru particularly preferred.

Numerous embodiments of the catalysts useful in the reactions of the disclosure are described in more detail infra. For the sake of convenience, the catalysts are described in groups, but it should be emphasized that these groups are not meant, to be limiting in any way. That is, any of the catalysts useful in the disclosure: may fit the description of more than one of the groups described herein.

A first group of catalysts, then, are commonly referred to as $1^{st}$ Generation Grubbs-type catalysts, and have the structure of formula (II). For the first group of catalysts, M and m are as described above, and n, $X^1$, $X^2$, $L^1$, $L^2$, $L^3$, $R^1$, and $R^2$ are described as follows.

For the first group of catalysts, n is 0, and $L^1$ and $L^2$ are independently selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether. Exemplary ligands are trisubstituted phosphines.

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, aryloxycarbonyl, $C_6$-$C_{24}$ acyl, $C_2$-$C_{24}$ acyloxy, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in tarn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments. $X^1$ and $X^2$ are each chloride.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, alkaryl, $C_6$-$C_{24}$ aralkyl, etc.), and functional groups. $R^1$ and $R^2$ may also be linked to form a cyclic group, which may be aliphatic or aromatic, and may contain, substituents and/or heteroatoms. Generally, such a cyclic group will contain 4 to 12, preferably 5, 6, 7, or 8 ring atoms.

In preferred catalysis, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined earlier herein. Most preferably, $R^2$ is phenyl or vinyl substituted with one or more moieties selected from methyl, ethyl, chloro, bromo, iodo, fluoro, nitro, dimethylamino, methyl, methoxy, and phenyl. Optimally, $R^2$ is phenyl or —C≡C(CH$_3$)$_2$.

Any two or more (typically two, three, or four) of $X^1$, $X^2$, $L^1$, $L^2$, $L^3$, $R^1$, and $R^2$ can be taken together to form a cyclic group, as disclosed, for example, in U.S. Pat. No. 5,312,940 to Grubbs et al. When any of $X^1$, $X^2$, $L^1$, $L^2$, $L_3$, $R^1$, and $R^2$ are linked to form cyclic groups, those cyclic groups may contain 4 to 12, preferably 4,5,6,7 or S atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

A second group of catalysis, commonly referred to as $2^{nd}$ Generation Grubbs-type catalysts, have the structure of formula (II), wherein $L^1$ is a carbene ligand having the structure of formula (III)

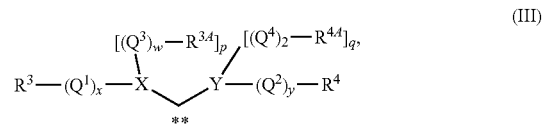

(III)

such that the complex may have the structure of formula (IV)

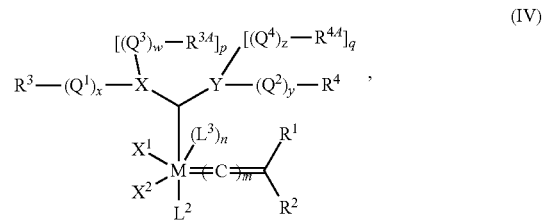

(IV)

wherein M, m, n, $X^1$, $X^2$, $L^2$, $L^3$, $R^1$, and $R^2$ are as defined for die first group of catalysts, and the remaining substituents are as follows.

X and Y are heteroatoms typically selected from N, O, S, and P. Since O and S are divalent, p is necessarily zero when X is O or S, and q is necessarily zero when Y is O or S. However, when X is N or P, then p is 1, and when Y is N or P, then q is 1. In a preferred embodiment, both X and Y are N.

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Preferably, w, x, y, and z are all zero. Further, two or more substituents on adjacent atoms within $Q^1$, $Q^2$, $Q^3$, and $Q^4$ may be linked to form an additional cyclic group.

$R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing Kg hydrocarbyl.

In addition, any two or more of $X^1$, $X^2$, $L^1$, $L^2$, $L^3$, $R^1$, $R^2$, $R^3$, $R^{3A}$, $R^4$, and $R^{4A}$ can be taken together to form a cyclic group, and any one or more of $X^1$, $X^2$, $L^1$, $L^2$, $L^3$, $R^1$, $R^2$, $R^3$, $R^{3A}$, $R^4$, and $R^{4A}$ may be attached to a support.

Preferably, $R^{3A}$ and $R^{4A}$ are linked to form a cyclic group so that the carbene ligand is an heterocyclic carbene and preferably an N-heterocyclic carbene, such as the N heterocylic carbene having the structure of formula (V)

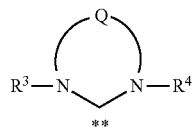

(V)

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents, Q is a linker, typically a hydrocarbylene linker, including substituted hydrocarbylene, heteroatom-containing hydrocarbylene, and substituted heteroatom-containing hydrocarbylene linkers, wherein two or mom substituents on adjacent atoms within Q may also be linked to form, an additional cyclic structure, which may be similarly substituted to provide a fused polycyclic structure of two to about five cyclic groups, Q is often, although again not necessarily, a two-atom linkage or a three-atom linkage.

Examples of N-heterocyclic carbene ligands suitable as $L^1$ thus include, but are not limited to, the following;

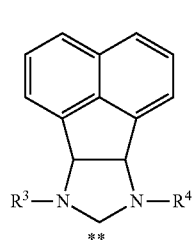 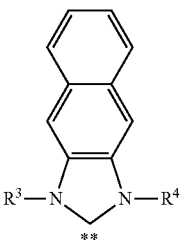

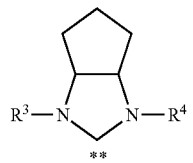 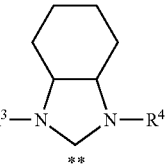

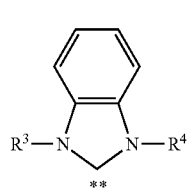 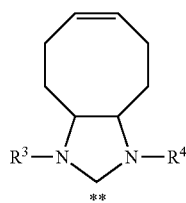

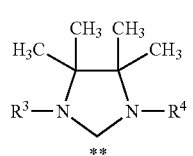 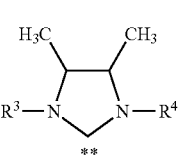

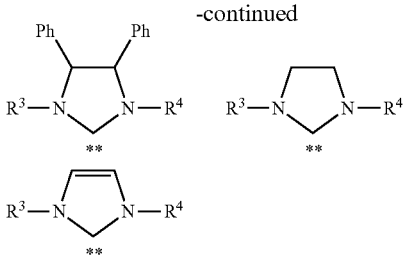

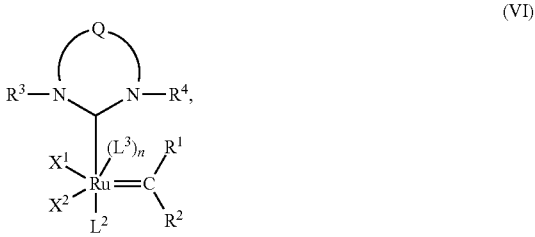

When M is ruthenium, then, the preferred complexes have the structure of formula (VI).

(VI)

In a more preferred embodiment, Q is a two-atom linkage having the structure —CR11R12—CR13R14— or CR11=CR13-, preferably —CR11R12—CR13R14—, wherein R11, R12, R13, and R14 are independently selected from hydrogen, hydrocarbyl, substituted hydrocarbyl, heteroatom-containing hydrocarbyl, substituted heteroatom-containing hydrocarbyl, and functional groups. Examples of functional groups here include carboxyl C1-C20 alkoxy, C5-C24 aryloxy, C2-C20 alkoxycarbonyl, C5-C24 alkoxycarbonyl, C2-C24 acyloxy, C1-C20 alkylthio, C5-C24 arylthio, C1-C20 alkylsulfonyl, and C1-C20 alkylsulfinyl, optionally substituted with one or more moieties selected from C1-C12 alkyl, C1-C12 alkoxy, C5-C14 aryl, hydroxyl, sulfhydryl, formyl, and halide. R11, R12, R13, and R14 are preferably independently selected from hydrogen, C1-C12 alkyl, substituted C1-C12 alkyl, C1-C12 heteroalkyl substituted C1-C12 heteroalkyl, phenyl, and substituted phenyl. Alternatively, any two of R11, R12, R13, and R14 may be linked together to form a substituted or unsubstituted, saturated or unsaturated ring structure, e.g., a C4-C12 alicyclic group or a C5 or C6 aryl group, which may itself be substituted, e.g., with linked or fused alicyclic or aromatic groups, or with other substituents.

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. As an example, $R^3$ and $R^4$ are mesityl.

In a third group of catalysts having the structure of formula (II), M, m, n, $X^1$, $X^2$, $R^1$, and $R^2$ are as defined for the first group of catalysts, $L^1$ is a strongly coordinating neutral electron donor ligand such as any of those described for the first and second group of catalysts, and $L^2$ and $L^3$ are weakly coordinating neutral electron donor ligands in the form of optionally substituted heterocyclic groups. Again, n is zero or 1, such that $L^3$ may or may not be present. Generally, in the third group of catalysts, $L^2$ and $L^3$ are optionally substituted five- or six-membered monocyclic groups containing 1 to 4, preferably 1 to 3, most preferably 1 to 2 heteroatoms, or are optionally substituted bicyclic polycyclic structures composed of 2 to 5 such five- or six-membered monocyclic groups. If the heterocyclic group is substituted. It should not be substituted on a coordinating heteroatom, and any one cyclic moiety within a heterocyclic group will generally not be substituted with more than 3 substituents.

For the third group of catalysts, examples of $L^2$ and $L^3$ include, without limitation, heterocycles containing nitrogen, sulfur, oxygen, or a mixture thereof.

Examples of nitrogen-containing heterocycles appropriate for $L^2$ and $L^3$ include pyridine, bipyridine, pyridazine, pyrimidine, bipyridazine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, biisoquinoline, cinnoline, quinazoline, naphthyridine, piperidine, piperazine, pyrrolidine, pyrazolidine, quinuclidine, imidazolidine, picolylamine, purine, benzimidazole, bisimidazole, phenazine, acridine, and carbazole.

Examples of sulfur-containing heterocycles appropriate for $L^2$ and $L^3$ include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thianthrene.

Examples of oxygen-containing heterocycles appropriate for $L^2$ and $L^3$ include 2H-pyran, 4H-pyran, 2-pyrone, 4-pyrone, 1,2-dioxin, 1,3-dioxin, oxepin, furan, 2H-1-benzopyran, coumarin, cumarone, chromene, chroman-4-one, isochromen-1-one, isochromen-3-one, xanthene, tetrahydrofuran, 1,4-dioxan, and dibenzofuran.

Examples of mixed heterocycles appropriate for $L^2$ and $L^3$ include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isoxazine, phenoxazine, phenothiazine, pyrano[3,4-b]pyrrole, indoxazine, benzoxazole, anthranil, and morpholine.

Preferred $L^2$ and $L^3$ ligands are aromatic nitrogen-containing and oxygen-containing heterocycles, and particularly preferred $L^2$ and $L^3$ ligands are monocyclic N-heteroaryl ligands that are optionally substituted with 1 to 3, preferably 1 or 2, substituents. Specific examples of particularly preferred $L^2$ and $L^3$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on $L^2$ and/or $L^3$ are selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, $C_6$-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamide, formyl, thioformyl, amino, mono-($C_1$-$C_{20}$ alkyl)-substituted-amino, di-($C_1$-$C_{20}$ alkyl)-substituted amino, mono-($C_5$-$C_{24}$ aryl)-substituted amino, di-($C_5$-$C_{24}$ aryl)-substituted amino, di-N—($C_1$-$C_{20}$ alkyl), N—($C_5$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on $L^2$ and $L^3$ include, without limitation, halo, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroaralkyl, $C_1$-$C_{12}$ alkoxy, $C_5$-$C_{14}$ aryloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_{14}$ aryl)-substituted amino, and nitro.

Of the foregoing, the most preferred substituents are halo, $C_1$-$C_6$ alkyl, $C_1$-$C_6$ haloalkyl, $C_1$-$C_6$ alkoxy, phenyl, substituted phenyl, formyl, N,N-di$C_1$-$C_6$ alkyl)amino, nitro, and nitrogen heterocycles as described above (including, for example, pyrrolidine, piperidine, piperazine, pyrazine, pyrimidine, pyridine, pyridazine, etc.).

$L^2$ and $L^3$ may also be taken together to form a bidentate or multidentate ligand containing two or more, generally two, coordinating heteroatoms such as N, O, S, or P, with preferred such ligands being diimine ligands of the Brookhart type. One representative bidentate ligand has the structure of formula (VII)

(VII)

wherein $R^{15}$, $R^{16}$, $R^{17}$, and $R^{18}$ hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), heteroatom-containing hydrocarbyl (e.g., $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or substituted heteroatom-containing hydrocarbyl (e.g., substituted $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or (1) $R^{15}$ and $R^{16}$, (2) $R^{17}$ and $R^{18}$, (3) $R^{16}$ and $R^{17}$, or (4) both $R^{15}$ and $R^{16}$, and $R^{17}$ and $R^{18}$, may be taken together to form a ring, i.e., an N-heterocycle. Preferred cyclic groups in such a case are five- and six-membered rings, typically aromatic rings.

In a fourth group of catalysts that have the structure of formula (I), two of the substituents are taken together to form a bidentate ligand or a tridentate ligand. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$—, —As(Ph)$_2$CH$_2$CH$_2$As(Ph$_2$)—, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$—, and —OC(CH$_3$)$_2$(CH$_3$)$_2$CO—. Preferred bidentate ligands are —P(Ph)$_2$CH$_2$CH$_2$P(Ph)$_2$- and —P(CH$_3$)$_2$(CH$_2$)$_2$P(CH$_3$)$_2$—. Tridentate ligands include, but are not limited to, (CH$_3$)$_2$NCH$_2$CH$_2$P(Ph)CH$_2$CH$_2$N(CH$_3$)$_2$. Other preferred tridentate ligands are those in which any three of $X^1$, $X^2$, $L^1$, $L^2$, $L^3$, $R^1$, and $R^2$ (e.g., $X^1$, $L^1$, and $L^2$) are taken together to be cyclopentadienyl indenyl, or fluorenyl, each optionally substituted with $C_2$-$C_{20}$ alkenyl, $C_2$-$C_{20}$ alkynyl, $C_1$-$C_{20}$ alkyl, $C_5$-$C_{20}$ aryl, $C_1$-$C_{20}$ alkoxy, $C_2$-$C_{20}$ alkenyloxy, $C_2$-$C_{20}$ alkynyloxy, $C_5$-$C_{20}$ aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl, each of which may be further substituted with $C_1$-$C_6$ alkyl, halide, $C_1$-$C_6$ alkoxy or with a phenyl group optionally substituted with halide, $C_1$-$C_6$ alkyl, or $C_1$-$C_6$ alkoxy. More, preferably, in compounds of this type, X, $L^1$ and $L^2$ are taken together to be cyclopentadienyl or indenyl, each optionally substituted with vinyl, $C_1$-$C_{10}$ alkyl, $C_5$-$C_{20}$ aryl $C_1$-$C_{10}$ carboxylate, $C_2$-$C_{10}$ alkoxycarbonyl, $C_1$-$C_{10}$ alkoxy, or $C_5$-$C_{20}$ aryloxy, each optionally substituted with $C_1$-$C_6$ alkyl, halide, $C_1$-$C_6$ alkoxy or with a phenyl group optionally substituted with halide, $C_1$-$C_6$ alkyl or $C_1$-$C_6$ alkoxy. Most preferably, X, $L^1$ and $L^2$ may be taken together to be cyclopentadienyl, optionally substituted with vinyl, hydrogen, methyl, or phenyl. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

Complexes wherein $L^2$ and $R^2$ are linked are examples of the fourth group of catalysts, and are commonly called "Grubbs-Hoveyda" catalysts. Examples of Grubbs-Hoveyda-type catalysts include the following:

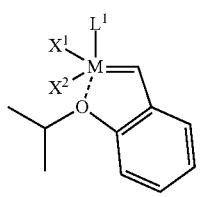
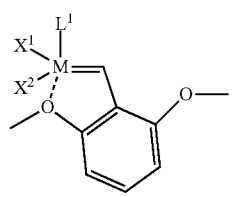

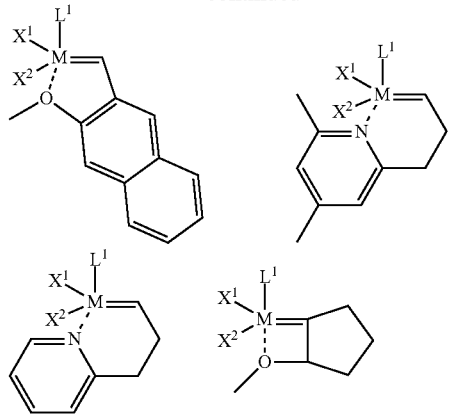

wherein $L^1$, $X^1$, $X^2$, and M are as described for any of the other groups of catalysts, In addition to the catalysts that have the structure of formula (II), as described above, other transition metal carbene complexes include, but are not limited to:

neutral ruthenium or osmium metal carbene complexes containing metal centers that are formally in the +2 oxidation state, have an electron count of 16, are penta-coordinated, and are of the general formula (VIII);

neutral ruthenium or osmium metal carbene complexes containing metal centers that are formally in the +2 oxidation state, have an electron count of 18, are hexa-coordinated, and are of the general formula (IX);

cationic ruthenium or osmium metal carbene complexes containing metal centers that are formally in the +2 oxidation state, have an electron count of 14, are tetra-coordinated, and are of the general formula (X); and cationic ruthenium or osmium metal carbene complexes containing metal centers that are formally in the +2 oxidation state, have an electron count of 14, are tetra coordinated, and are of the general formula (XI)

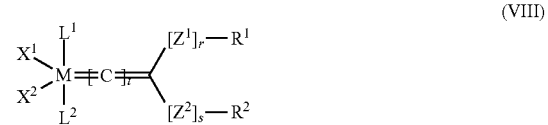
(VIII)

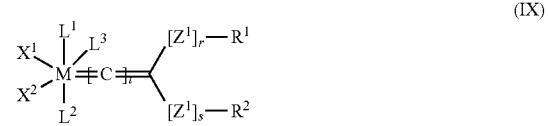
(IX)

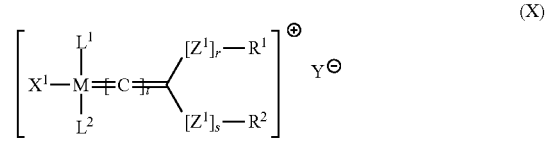
(X)

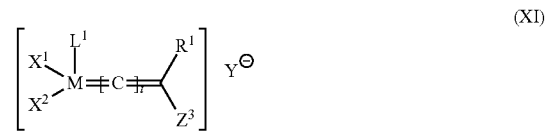
(XI)

wherein: $X^1$, $X^2$, $L^1$, $L^2$, n, $L^3$, $R^1$, and $R^2$ are as defined for any of the previously-defined four groups of catalysts; r and s are independently zero or 1; t is an integer in the range of zero to 5; Y is any non-coordinating anion (e.g., a halide ion, $BF_4^-$, etc.); $Z^1$ and $Z^2$ are independently selected from —O—, —S—, —$NR^2$—, —$PR^2$—, —P(=O)$R^2$—, —P(O$R^2$)—, —P(=O)(O$R^2$)—, —C(=O)—, —C(=O)O—, —OC(=O)—, —OC(=O)O—, —S(=O)—, and —S(=O)$_2$—; $Z^3$ is any cationic moiety such as —P($R^2$)$_3^+$ or —N($R^2$)$_3^+$; and any two or more of $X^1$, $X^2$, $L^1$, $L^2$, $L^3$, n, $Z^1$, $Z^2$, $Z^3$, $R^1$, and $R^2$ may be taken together to form a cyclic group, e.g., a multidentate ligand, and wherein any one or more of $X^1$, $X^2$, $L^1$, $L^2$, n, $L^3$, $Z^1$, $Z^2$, $Z^3$, $R^1$, and $R^2$ may be attached to a support, As is understood in the field of catalysis, suitable solid supports for any of the catalysts described herein may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect, if indirect, typically through a functional group on a support surface.

Non-limiting examples of catalysts that may be used in the reactions of the disclosure include the following, some of which for convenience are identified throughout this disclosure by reference to their molecular weight:

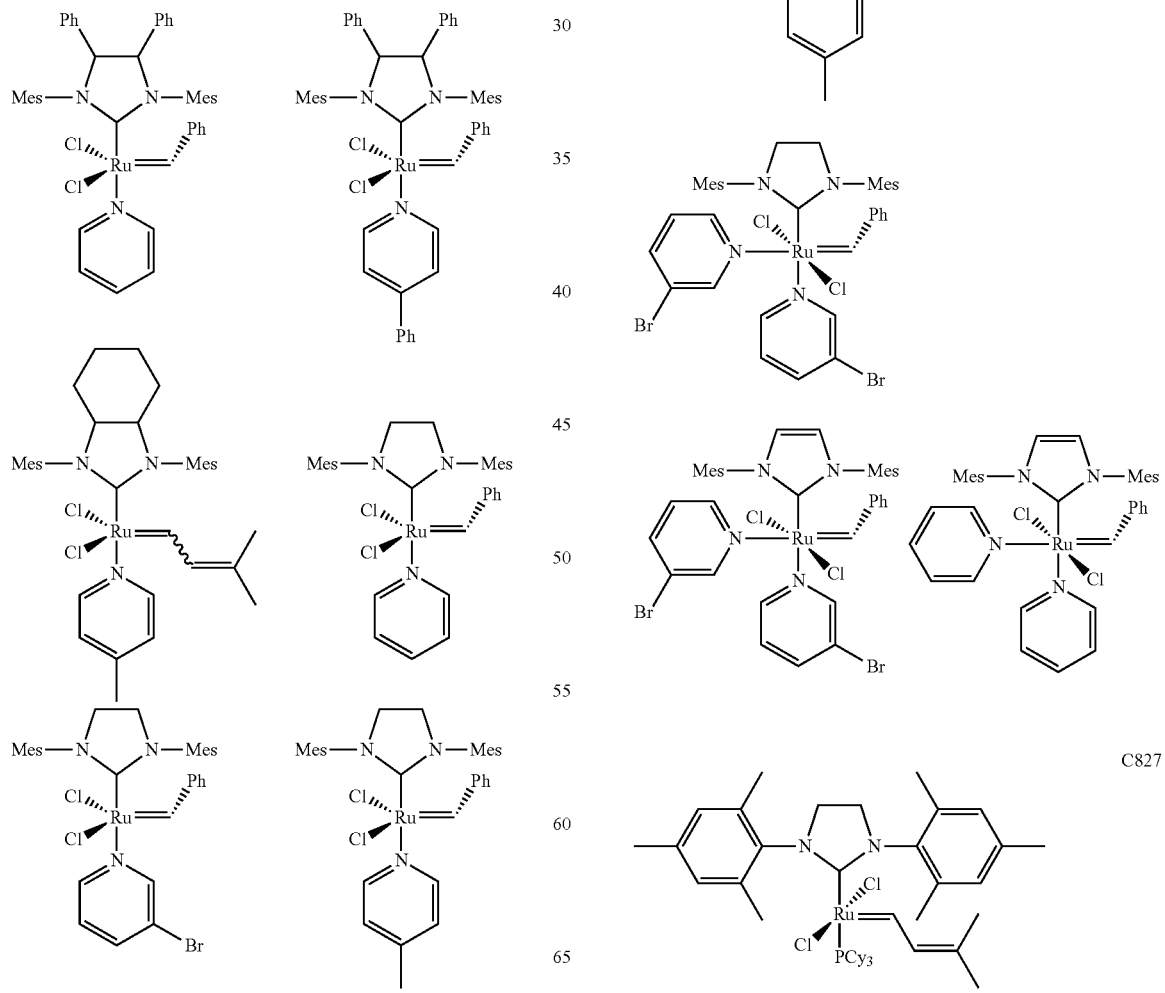

-continued
C859
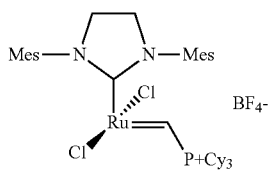
C841-n
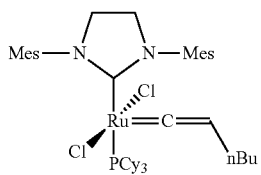
C916
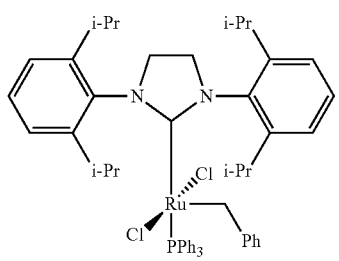
C965-p
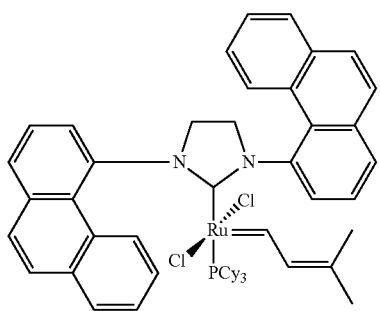
C727
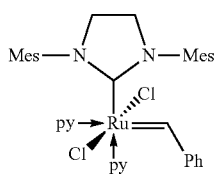
C577
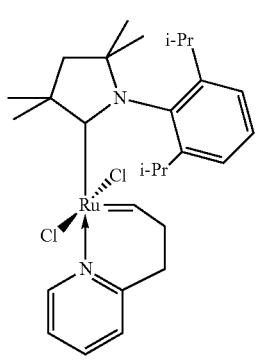
-continued
C646
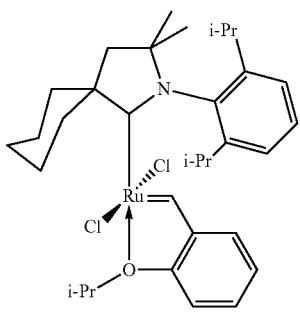
C701
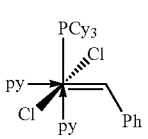
C767-m
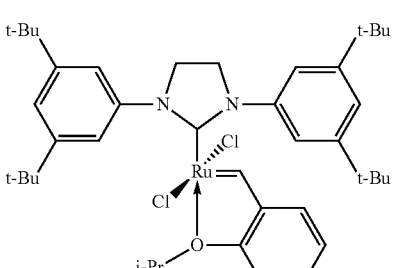
C811
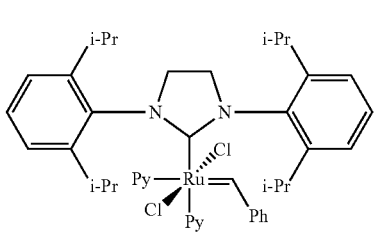
C801
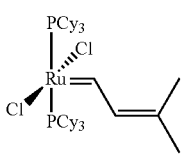
C838
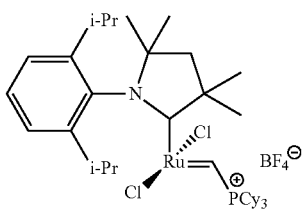
C712
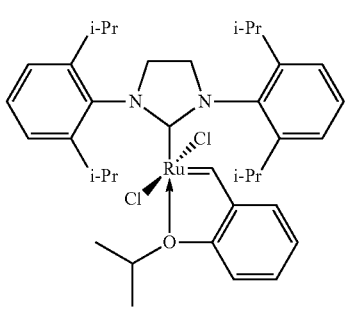

C933
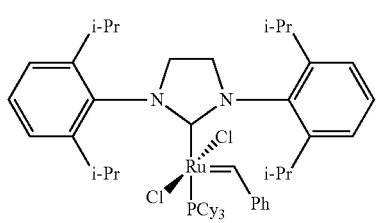
C824
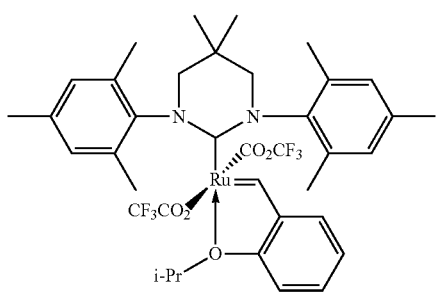
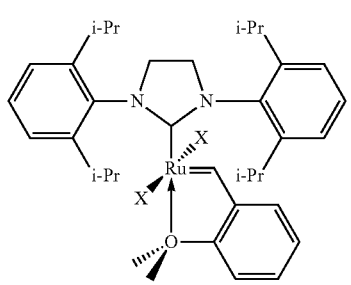
C697 (X = Cl)
C785 (X = Br)
C879 (X = I)
C601
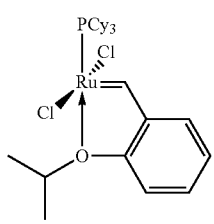
C848
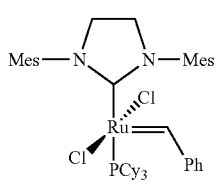
C831
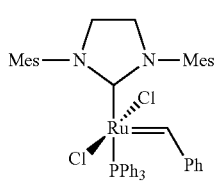
C627
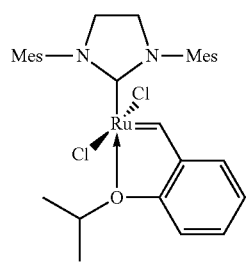
C672
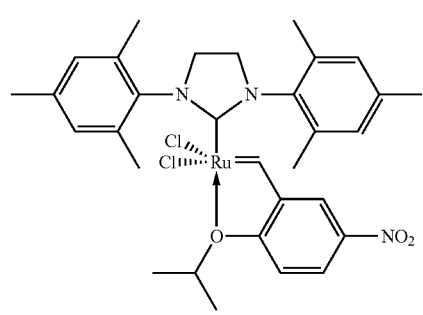
C657
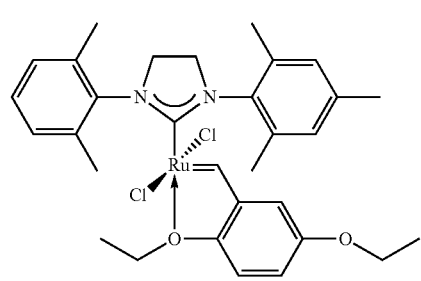
C734
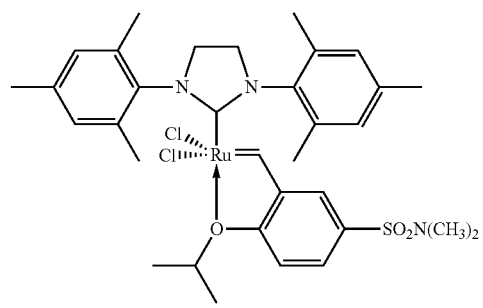
C767
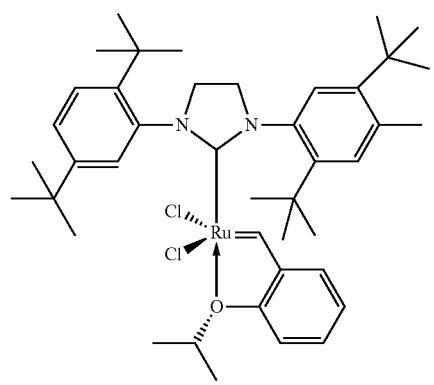

C809
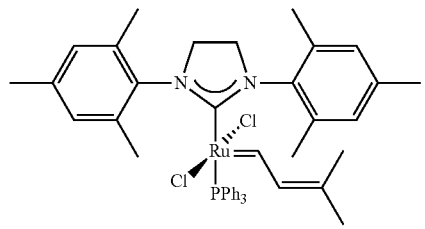
C849
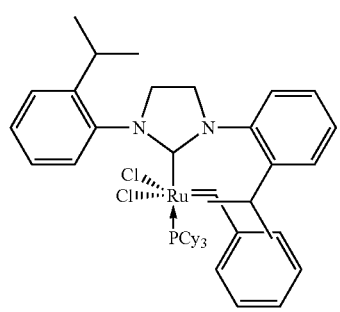
C923
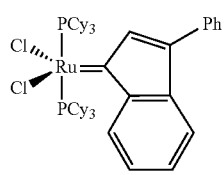
C-524
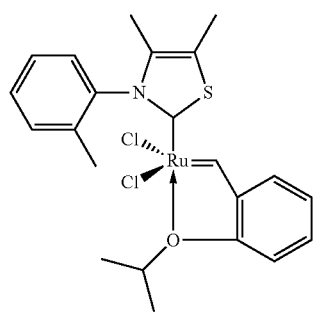
C-552
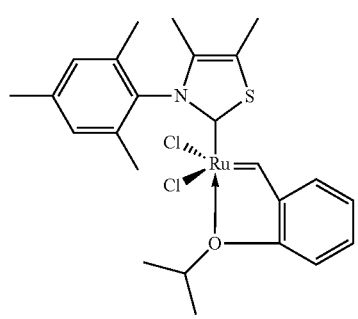
C-566
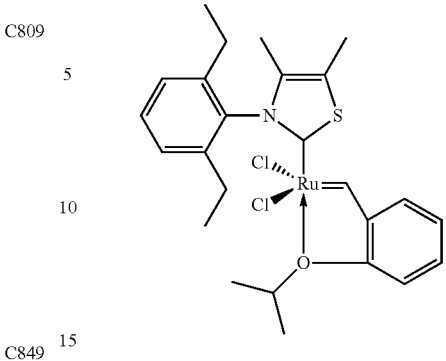
DPAI-278
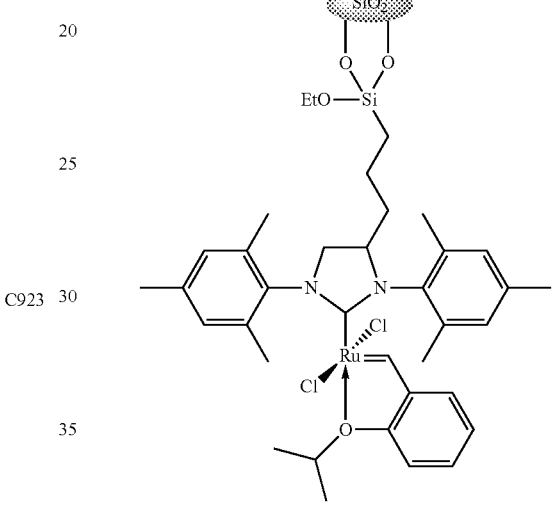
C-598
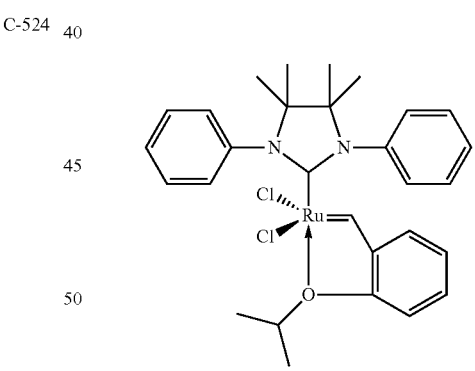
C-626
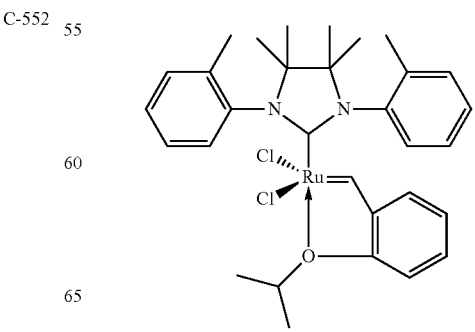

C949
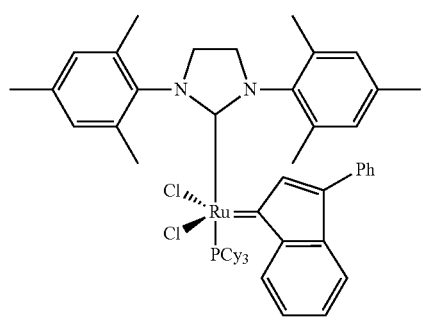
C823
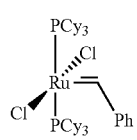
C606
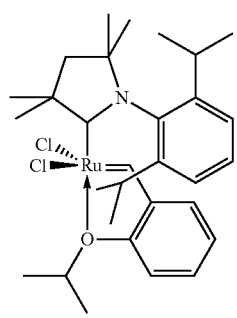
C629
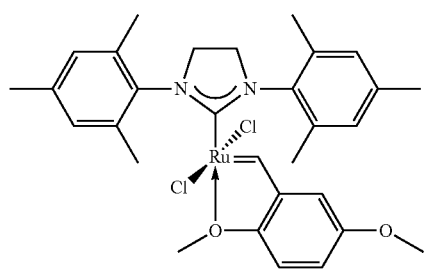
C833
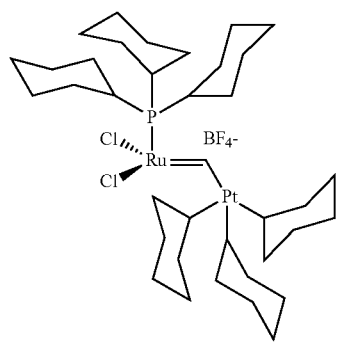
C613
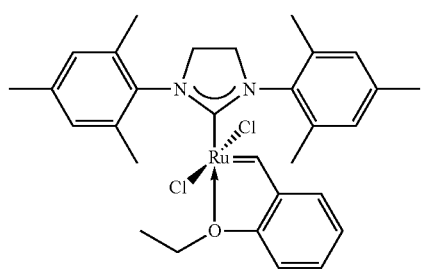
C827
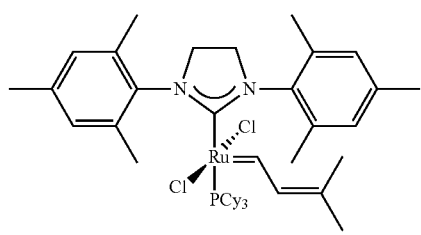
C627
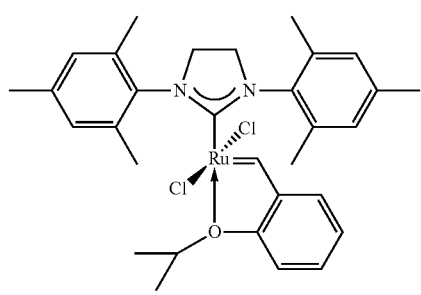
C793
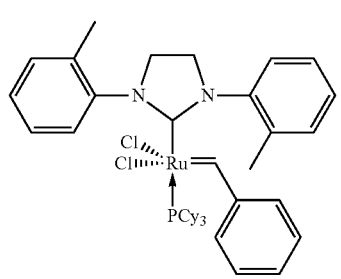
C598Cs
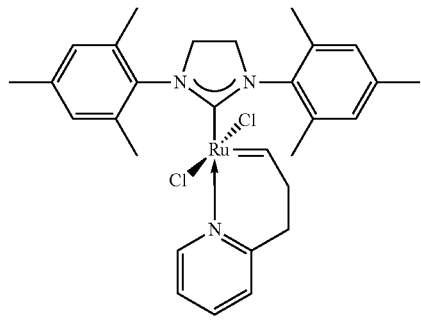

-continued

C782
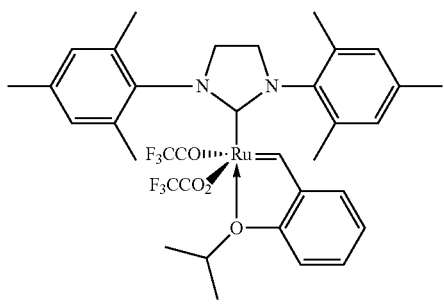

C702
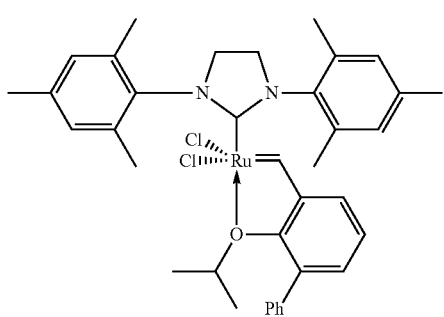

C884
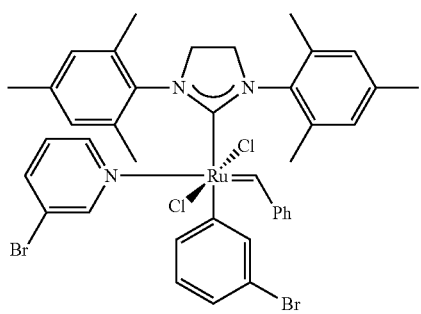

C933
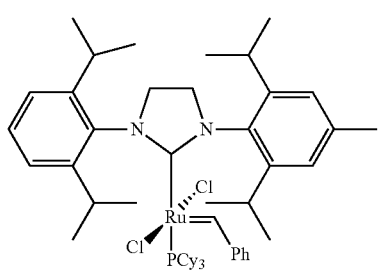

C866
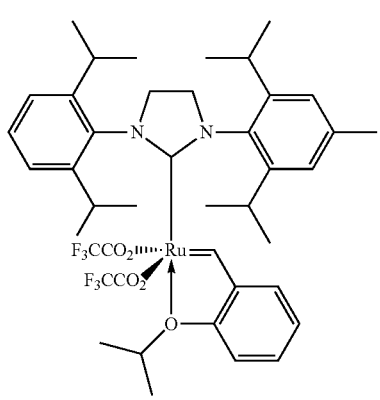

-continued

C571
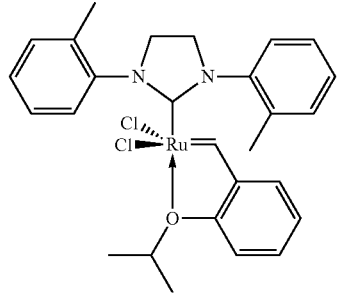

C578
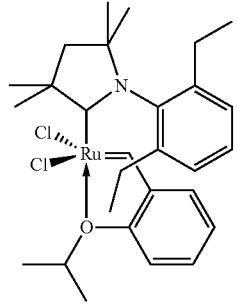

In the foregoing molecular structures and formulae, Ph represents phenyl, Cy represents cyclohexane, Me represents methyl, nBu represents s-butyl, i-Pr represents isopropyl, py represents pyridine (coordinated through the N atom), and Mes represents mesityl (i.e., 2,4,6-trimethylphenyl).

Further examples of catalysts useful in the reactions of the present disclosure include the following: ruthenium (II) dichloro (3-methyl-1,2-butenylidene)bis(tricyclopentylphosphine) (C716); ruthenium (II) dichloro (3-methyl-1,2-butenylidene)bis(tricyclohexylphosphine) (C801); ruthenium (II) dichloro (phenylmethylene)bis(tricyclohexylphosphine) (C823); ruthenium (II) [1,3-bis-(2,4,6-trimethylphenyl)-2-imidazolidinylidene)dichloro (phenylmethylene) (triphenylphosphine) (C830), and ruthenium (II) dichloro (vinyl phenylmethylene)bis(tricyclohexylphosphine) (C835); ruthenium (II) dichloro (tricyclohexylphosphine) (o-isopropoxyphenylmethylene) (C601), and ruthenium (II) (1,3-bis-(2,4,6,-trimethylphenyl)-2-imidazolidinylidene) dichloro (phenylmethylene) (bis 3-bromopyridine (C884).

The transition metal complexes used as catalysts herein can be prepared by several different methods, such as those described by Schwab et al. (1996) J. Am. Chem. Soc. 118: 100-11.0, Scholl et al. (1999) Org. Lett. 6:953-956, Sanford et al. (2001) J. Am. Chem., Soc. 123:749-750, U.S. Pat. No. 5,312,940 and U.S. Pat. No. 5,342,909. Also see U.S. Patent Publication No. 2003/0055262 to Grubbs et al. filed Apr. 16, 2002 for "Group 8 Transition Metal Carbene Complexes as Enantioselective Olefin Metathesis Catalysts", International Patent Publication No. WO 02/079208 application Ser. No. 10/115,581 to Grubbs, Morgan, Benitez, and Louie, filed Apr. 2, 2002, for "One-Pot Synthesis of Group 8 Transition Metal Carbene Complexes Useful as Olefin Metathesis Catalysts," commonly assigned herewith to the California Institute of Technology, Preferred synthetic methods are described in International Patent Publication No. WO 03/11455A1 to Grubbs et al. for "Hexacoordinated Ruthenium or Osmium Metal Carbene Metathesis Catalysts," published Feb. 13, 2003.

The components of the reactions of the present disclosure may be combined in any order, and it will be appreciated that the order of combining the reactants may be adjusted as needed. For example, the olefinic substrate may be added to the cross-metathesis partner, followed by addition of the catalyst. Alternatively, the olefinic substrate and cross-metathesis partner may be added to the catalyst. When one of the reactants is a gas, it may be necessary to add the catalyst to the liquid or solid reactant before introducing the gaseous reactant.

The catalyst may be added to the reaction either as a solid, dissolved in one of the reactants, or dissolved in a solvent. The catalyst may be added in any quantity and manner effective for the intended results of the reaction. For example, predetermined amounts of catalyst can be sequentially added to the reaction mixture at predetermined time intervals.

The reactions of the present disclosure may be carried out in a solvent, and any solvent that is inert towards cross-metathesis may be employed. Generally, solvents that may be used in the cross-metathesis reactions include organic, protic, or aqueous solvents, such as aromatic hydrocarbons, chlorinated hydrocarbons, ethers, aliphatic hydrocarbons, alcohols, water, or mixtures thereof. Example solvents include benzene, toluene, p-xylene, methylene chloride, 1,2-dichloroethane, dichlorobenzene, chlorobenzene, tetrahydrofuran, diethylether, pentane, methanol, ethanol, water, or mixtures thereof. In a preferred embodiment, the reactions of the present disclosure are carried out neat, i.e., without the use of a solvent.

It will be appreciated that the temperature at which a cross-metathesis reaction according to the present disclosure is conducted can be adjusted as needed, and may be at least about $-78°$ C., $-40°$ C., $-10°$ C., $0°$ C., $10°$ C., $20°$ C., $25°$ C., $35°$ C., $50°$ C., $100°$ C., or $150°$ C.

The product(s) of the cross-metathesis reactions according to the present disclosure can be purified by any of the methods commonly known and used in the art, including, for example, distillation and crystallization. It wilt be appreciated that any excess of cross-metathesis partner (e.g., alpha-olefin) after fee reaction is completed can be separated from, the final reaction mixture and recycled. Furthermore, any internal olefins present in the final reaction mixture can be separated, optionally purified, and recycled or used in a different reaction. It will also be appreciated that a mixture of terminal olefins and internal olefins (e.g., terminally unsaturated esters and internally unsaturated esters) produced, by the processes described herein can be separated from the final reaction mixture and used in a subsequent reaction. For example, such products may fee used in another metathesis process (e.g., a metathesis process wherein the terminally unsaturated esters and internally unsaturated esters are converted into diesters).

I. First Aspect—Cross-Metathesis Method at a Temperature of at Least 35° C.:

According to a first aspect, the reaction is carried out by contacting the at least one internal olefin with the cross metathesis partner in the presence of the metathesis catalyst under reaction conditions effective to allow cross-metathesis to occur, wherein the reaction conditions include a reaction temperature of at least 35° C. The reactants, catalysts and reactions conditions, described supra in the methods, compositions and reaction systems section, otherwise apply also for this aspect.

II. Second Aspect—Reaction under Inert Atmosphere with Ultra-Low Catalyst Loading According to a second aspect, the reaction is carried out by contacting, under an inert atmosphere and in the presence of a ruthenium alkylidene metathesis catalyst, an olefinic substrate comprised of at least one internal olefin with a cross metathesis partner comprised of an alpha olefinic reactant, under reaction conditions effective-to allow cross-metathesis to occur, wherein the catalyst is present in an amount ranging from about 1 ppm to about 50 ppm relative to the number of olefinic substrate double bonds. Generally, preferred catalyst amounts of about 1 to 10 ppm can be used for reactions with substrates with a level of peroxide <1 ppm and 15 ppm to 50 ppm for substrates with higher level of peroxide. The reactants, catalysts and reactions conditions, described supra in the methods, compositions and reaction systems section, otherwise apply also for this aspect.

III. Third Aspect—Reaction in Oxygen-Containing Atmosphere with Low Loading

According to a third aspect, the reaction is carried out by contacting, in an oxygen-containing atmosphere and in the presence of a ruthenium alkylidene metathesis catalyst, an olefinic substrate comprised of at least one internal olefin with a cross metathesis partner comprised of an alpha olefinic reactant, under reaction conditions effective to allow cross-metathesis to occur, wherein the catalyst is present in an amount ranging from about 50 ppm to about 100 ppm relative to the number of olefinic substrate double bonds. The reactants, catalysts and reactions conditions, described supra in the methods, compositions and reaction systems section, otherwise apply also for this aspect.

IV. Fourth Aspect—Reaction of Unpurified Mixtures of Internal Olefins under Inert Atmosphere, According to a fourth aspect, the reaction is carried out by contacting, under an inert atmosphere and in the presence of a ruthenium alkylidene metathesis catalyst, an olefinic substrate comprised of a mixture of monoglycerides, diglycerides, and triglycerides, with a cross metathesis partner comprised of an alpha olefinic reactant, under reaction conditions effective to allow cross-metathesis to occur. The reactants, catalysts and reactions conditions, described supra in the methods, compositions and reaction systems section, otherwise apply also for this aspect.

V. Fifth Aspect—Selecting Cross-Metathesis Partner in which the Alpha Olefin has a Solubility of at Least 0.25 M According to a fifth aspect, the reaction is carried out by contacting, in the presence of a ruthenium alkylidene metathesis catalyst, an olefinic substrate, comprised of at least one internal olefin with a cross metathesis partner. The cross metathesis partner is comprised of an alpha olefinic reactant having a solubility of at least 0.25 M in the olefinic substrate when each of the olefinic substrate and the alpha olefin are in liquid form. The contacting is performed under reaction conditions to allow cross-metathesis to occur. The reactants, catalysts and reactions conditions, described supra in the methods, compositions and reaction systems section, otherwise apply also for this aspect, VI. Sixth Aspect—Reactants Used in Molar ratios of 1 to 9 Compared to the Internal Olefin.

According to a sixth aspect, the reaction is carried out by contacting, under an inert atmosphere and in the presence of a ruthenium alkylidene metathesis catalyst, an olefinic substrate comprised of at least one internal olefin with a cross metathesis partner comprised of an alpha olefinic reactant, under reaction conditions effective to allow cross-metathesis to occur, wherein the moles of the olefinic substrate is approximately equal to 1 to 9 times the moles of the cross-metathesis partner. The reactants, catalysts and reactions conditions, described supra in the methods, compositions and reaction systems section, otherwise apply also for this aspect.

VII. Seventh Aspect—Reaction Mixtures for Carrying Out the Reactions

According to a seventh aspect, the reaction is carried out by contacting, in the presence of a ruthenium alkylidene metathesis catalyst an olefinic substrate comprised of at least one internal olefin with a cross metathesis partner comprised of an alpha olefinic reactant, under reaction conditions effective to ensure that the olefinic substrate and the cross-metathesis partner are in liquid form and to allow cross-metathesis to occur. The reactants, catalysts and reactions conditions, described supra in the methods, compositions and reaction systems section, otherwise apply also for this aspect.

VIII. Eighth Aspect—Mediation of Process with the Grubbs-Hoveyda Catalyst

According to an eighth aspect, the reaction is carried out by contacting, under an inert atmosphere and in the presence of a ruthenium alkylidene metathesis catalyst, an olefinic substrate comprised of at least one internal olefin with a cross metathesis partner comprised of an alpha olefinic reactant, under reaction conditions effective and to allow cross-metathesis to occur, wherein the catalyst is a Grubbs-Hoveyda-type catalyst. The reactants, catalysts and reactions conditions, described supra in the methods, compositions and reaction systems section, otherwise apply also for this aspect.

IX. Ninth Aspect—Olefinic Substrate Including Internal Olefin with High Molecular Weight According to a ninth aspect, the reaction is carried out by contacting, under an inert atmosphere and in the presence of a ruthenium alkylidene metathesis catalyst, an olefinic substrate comprised of at least one internal olefin with a cross metathesis partner comprised of an alpha olefinic reactant, with a cross metathesis partner comprised of an alpha olefinic reactant, under reaction conditions effective and to allow cross-metathesis to occur, wherein the internal olefin has a molecular weight (MW) of at least 250 g/mol, and/or is at least 15 carbon atom. Preferably the internal olefin has a molecular weight from about 300 g/mol to about 1000 g/mol and/or from 20 to 60 carbons.

Such high-MW internal olefin substrates can include readily available, inexpensive olefins or mixtures of olefins such as unsaturated or polyunsaturated triacylglycerides obtained from plant or animal oils, high-boiling petrochemical fractions, or elastomeric or other unsaturated polymers (e.g., polybutadienes or polyisoprenes). Mixtures of such high-MW olefins are typically difficult to separate due to their high boiling points and relatively similar toiling point ranges. They can also be difficult to purify because of the high temperatures required for distillation. Cross-metathesis of these high-MW substrates can be efficiently performed with alpha-olefins, especially lower alpha-olefins, to produce lower-MW products that can be more easily separated and/or purified. In preferred embodiments, the high-MW internal olefin substrate is a triacylglyceride or a mixture of triacylglycerides. Such compounds could be saponified to mixtures of lower-MW FAMEs, although such mixtures are still difficult to separate. If mixed FAMEs are used as substrates for cross-metathesis, very complex mixtures of products are obtained. However, cross-metathesis of triacylglycerides can be efficiently performed with alpha-olefins. By proper selection of the alpha-olefin, in particularly using lower alpha-olefins such as propene or butene, relatively low-MW hydrocarbon olefins are produced that can be easily separated from the metathesized triacylglyceride fragment, in a subsequent step, the remaining triacylglyceride fragment can be saponified to yield unsaturated carboxylate compounds, The reactants, catalysts and reactions conditions, described supra in the methods, compositions and reaction systems section, otherwise apply also for this aspect.

X. Tenth Aspect—Reaction Mixtures Under a Pressure Slightly Above Atmospheric

According to a tenth aspect, the reaction is carried out by contacting, in the presence of a ruthenium alkylidene metathesis catalyst, comprised of at least one internal olefin with a cross metathesis partner comprised of an alpha olefinic reactant, under a pressure equal to or greater than 1.1 atm and typically below 14 atms and under reaction conditions effective to allow cross-metathesis to occur. Preferred pressures are typically <14 atms for reactions wherein the alpha olefinic reactant is 1-propene, typically <4 atms for reactions wherein the alpha olefinic reactant is 1-butene and typically <2 atms for reactions wherein the alpha olefinic reactant is 1-pentene to 1-eicosene. The reactants, catalysts and reactions conditions, described supra in the methods, compositions and reaction systems section, otherwise apply also for this aspect.

It is to be understood, that while the methods and composition of the present disclosure have been described in conjunction with the preferred specific aspects thereof, that the description above as well as the examples that follow are intended to illustrate and not limit the scope of the disclosure. Other aspects, advantages, and modifications within the scope of the disclosure will be apparent: to those skilled in the art to which the disclosure pertains.

Experimental

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at, near atmospheric pressure or slightly above atmospheric pressure (equal or greater than 1.1 atm).

EXAMPLES

General Procedures:

Ethenolyses: Ethenolyses of olefinic substrates were set up under an inert atmosphere in a glove box. As an example reaction procedure, a Fisher-Porter bottle equipped with a stir bar was charged with methyl oleate (>99%) from Nu-Check-Prep (Elysian, Minn.) (15.0 g; 50.6 mmol). A solution of olefin metathesis catalyst of an appropriate concentration was prepared in anhydrous dichloromethane (from Aldrich) and the desired volume of this solution added to the methyl oleate. The head of the Fisher-Porter bottle was equipped with a pressure gauge and a dip-tube was adapted on the bottle. The system was sealed and taken out of the glove box to an ethylene line. The vessel was then purged 3 times with ethylene (Polymer purity 99.9% from Matheson Tri Gas), pressurised to the indicated pressure and placed in an oil bath at the indicated temperature. The reaction was monitored by collecting samples into vials at different reaction times via the dip-tube. Immediately after collecting a sample, the reaction was stopped by adding 1 ml, of a 1.0 M isopropanol solution of tris-hydroxymethylphopshine (THMP) to the vial. The samples were then heated for at least 1 hour at 60° C., diluted with 1 mL of distilled water, extracted with 1 mL of hexanes and analysed by gas chromatography (GC). If the olefinic substrate is a glyceride, it is transesterified prior to GC analysis using a method similar to the transesterification of metathesized SBO described below.

General Procedure for the Cross-Metatheses of Olefinic Substrate and Alpha-Olefin:

Terminal olefins were synthesized by the cross metathesis of short chained alpha-olefins and seed oils with a ruthenium metathesis catalyst. The short chained alpha-olefins include olefins preferably having 8 or less carbon atoms, such as 1-propene, 1-butene, 1-pentene, etc. but >9 carbon alpha-olefins are acceptable. Seed oils include triacylglycerides, as in soybean oil, fatty acid esters, as in jojoba oil and FAMES, such as methyl esters of soybean oil (soy FAME).

When the alpha-olefin used was a gas under ambient conditions (e.g. 1-propene and 1-butene), a procedure analogous to that used for the ethenolyses was also employed. As such, a Fisher-Porter bottle equipped with a stir bar was charged with the olefinic substrate. A solution of olefin metathesis catalyst of an appropriate concentration was prepared in anhydrous dichloromethane (from Aldrich) and the desired volume of this solution added to the olefinic substrate. The head of the Fisher-Porter bottle was equipped with a pressure gauge and a dip-tube was adapted on the bottle. The system was sealed and taken out of the glove box to a gas line. The vessel was then purged 3 times with the gas (e.g., 1-propene and 1-butene), pressurized to the indicated pressure (about 50 to about 150 psi for 1-propene and about 30 to about 90 psi for 1-butene) and placed in an oil bath at the indicated temperature. The reaction was monitored by following the method described above. When the alpha-olefin used was a liquid under ambient conditions (e.g., 1-octene), the olefinic substrate and the alpha-olefin were mixed in an oven-dried 20 mL vial equipped with a stir bar. The vial was sealed with a Teflon-seal cap and the olefinic substrate/alpha-olefin mixture was brought to the indicated temperature, so that the reactions are conducted under a slightly positive pressure (from 1.1 to about 2 atm, i.e. from 16 psi to about 30 psi). A solution of olefin metathesis catalyst of an appropriate concentration was prepared in anhydrous dichloromethane (from Aldrich) and the desired volume of this solution added to the olefinic substrate/alpha-olefin mixture via syringe through the Teflon-seal while stirring. The reaction mixture was kept at the desired temperature for the indicated period of time before adding a 1.0 M solution of THMP (1 mL) via syringe through the Teflon-seal cap. The mixture was then heated at 60° C. for 1 hour, diluted with 5 mL of distilled water and 5 mL of hexanes and the organic phase was separated and analyzed by GC. If the olefinic substrate is a glyceride, it is transesterified prior to GC analysis using a method similar to the transesterification of metathesized SBO described below.

Example Procedure for the Transesterification of Metathesized SBO

A glass 3-necked round bottom flask containing a magnetic stirrer and fitted with a condenser, temperature probe, and gas adapter was charged with crude metathesized SBO product (~2 L) and 1% w/w NaOMe in MeOH. The resulting light yellow heterogeneous mixture was stirred at 60° C. for 1 hr. Towards the end of the hour, the mixture turned a homogeneous orange color, Esterified products were transferred into a separately funnel and extracted with 2.0 L DI-$H_2O$. The aqueous layer was then extracted with 2×2.0 L. $Et_2O$. The combined organic extracts were dried over anhydrous $Na_2SO_4$ (300 g) for 20 hours. The solution of esterified products was filtered and the filtrate was stripped of solvent we rotary evaporator.

Vacuum Distillation A glass 2.0 L 3-necked round bottom flask with a magnetic stirrer, packed column, distillation head, and temperature controller was charged with methyl ester products and placed in a heating mantle. The flask was attached to a 2-inch×36-inch glass distillation packed column contain 0.16" Pro-Pak™ stainless steel saddles. The distillation column was adapted to a fractional distilling head, which was connected to a vacuum line. A 500 mL pre-weighed round bottom flask was used for collecting the fractions. Vacuum on this system was <1 mmHg.

GC Analysis Conditions The products were analyzed using an Agilent 6890 gas chromatography (GC) instrument with a flame ionization detector (FID). The following conditions and equipment were used:

Column: Rtx-5, 30 m×0.25 mm (ID)×0.25 μm film thickness.
Manufacturer: Restek
GC and column conditions: Injector temperature; 250° C. Detector temperature: 280° C.
Oven temperature: Starting temperature: 100° C., held time: 1 minute.
Ramp rate 10° C./min to 250° C., hold time: 12 minutes.
Carrier gas: Helium
Mean gas velocity: 31.3±3.5% cm/sec (calculated)
Split ratio: ~50:1

The products were characterized by comparing peaks with known standards, in conjunction with supporting data from mass spectrum analysis (GCMS-Agilent 5973N), GCMS analysis was accomplished with a second Rtx-5, 30 m×0.25 mm (ID)×0.25 μm film thickness GC column, using the same method as above.

Table 1 provides GC retention times used for identifying compounds in the examples provided below. Table 1 also provides compound abbreviations that are used throughout the examples.

TABLE 1

GC Analysis of Products from the Cross Metathesis of Seed Oils with 1-Propene and 1-Butene

| Retention Time (min) | Compound | Compound Abbreviation |
|---|---|---|
| 1.300 | E-2-Octene | $2C_8$ |
| 1.596 | 3-Nonene | $3C_9$ |
| 2.039 | 1-Decene | $1C_{10}$ |
| 2.907 | E-2-Undecene | $E-2C_{11}$ |
| 3.001 | Z-2-Undecene | $Z-2C_{11}$ |
| 3.836 | 3-Dodecenes | $3C_{12}$ |
| 5.298 | Methyl 9-Decenoate | $9C_{10}O_2Me$ (9DA) |
| 6.708 | Methyl E-9-Undecenoate | $E-9C_{11}O_2Me$ (9UDA) |
| 6.852 | Methyl Z-9-Undecenoate | $Z-9C_{11}O_2Me$ (9UDA) |
| 7.419 | Pentadecadienes | $nC_{15}$ |
| 7.816 | Methyl E-9-Dodecenoate | $E-9C_{12}O_2Me$ |
| 7.894 | Methyl Z-9-Dodecenoate | $Z-9C_{12}O_2Me$ |
| 10.939 | 9-Octadecene | $9C_{18}$ |
| 11.290 | Methyl 9-12 tetradecadienoate | $9,12C_{14}O_2Me$ |
| 12.523 | Methyl palmitate | $C_{16}O_2Me$ |
| 14.306 | Methyl linoleates | $9,12C_{18}O_2Me$ |
| 14.363 | Methyl oleates | $9C_{18}O_2Me$ |
| 14.537 | Methyl stearate | $C_{18}O_2Me$ |
| 17.138 | Methyl 9,21-Henicosadienaote | $9,12C_{18}O_2Me$ |
| 17.586 | 1,18 Dimethyl ester of 9-Octadecene | $9,12C_{18}O_2Me$ |
| 22.236 | Methyl 9,12,15-docosatrienoate | $9,12,15C_{21}O_2Me$ |

Example 1

Ethenolysis of Different Oils

Different triglycerides and fatty acid methyl esters (FAMEs) were subjected to the ethenolysis procedure (vide supra). Methyl oleate (MO), >99% was obtained from Nu-Check-Prep (Elysian, Minn.). Soybean oil (SBO), salad-grade (i.e., refined, bleached, deodorized) was obtained from Cargill. Soy FAME, not distilled and canola FAME, distilled were obtained from Cognis. All oils were degassed by sparging with argon for 1 hour/L prior to being stored over activated alumina in a glove box under an argon atmosphere. The results are provided in Table 2.

TABLE 2

Ethenolysis of Different Oils

| Entry | Oil | Temp. (° C.) | Pressure (psi) | Time (hr) | Catalyst (Loading) | 9DA GC Area (%) | TON$_{9DA}$ |
|---|---|---|---|---|---|---|---|
| 1 | MO | 40 | 150 | 4 | C823 (10 ppm) | 7.8 | 7,800[3] |
| 2 | MO | 60 | 150 | 2 | C827 (100 ppm) | 24.2 | 2,400 |
| 3 | MO | 40 | 150 | 4 | C827 (10 ppm) | 0.6 | 600 |
| 4 | SBO | 40 | 100 | 6 | C823 (111 ppm) | 16.1 | 1,450 |
| 5 | SBO | 40 | 150 | 6 | C827 (10 ppm) | 0.3 | 300 |
| 6 | SBO | 40 | 150 | 6 | C627 (22 ppm) | 6.4 | 2,910 |
| 7 | SBO | 40 | 150 | 6 | C712 (22 ppm) | 10.6 | 4,820 |
| 8 | Soy FAME | 40 | 150 | 4 | C823 (67 ppm) | 13.3 | 1,985 |
| 9 | Soy FAME | 40 | 150 | 4 | C827 (10 ppm) | 1.2 | 1,200 |
| 10 | Soy FAME | 40 | 150 | 4 | C712 (10 ppm) | 4.9 | 4,900 |
| 11 | Canola FAME | 40 | 150 | 4 | C823 (71 ppm) | 16.0 | 2,250 |
| 12 | Canola FAME | 40 | 150 | 4 | C827 (10 ppm) | 0.4 | 400 |
| 13 | Canola FAME | 40 | 150 | 4 | C712 (10 ppm) | 2.6 | 2,600 |

[1] 9DA GC Area (%) is the area percentage of methyl-9-decenoate (9DA) on GC chromatogram
[2] TON$_{9DA}$ (turn-over number based on 9DA only) = 10,000 * [9DA GC Area (%)]/[catalyst loading (ppm)]
[3] The TON$_{9DA}$ corresponds to about half of the ethenolysis turnover number, because the TON$_{9DA}$ only takes the GC area percentage of half of the products (i.e., 9DA) into consideration. Therefore, this TON$_{9DA}$ of 7,800 corresponds to an ethenolysis turnover number of about 15,600, which is similar to the 15,400 ethenolysis turnover number reported by Maughon and coworkers (*Organometallics* 2004, 23, 2027-2047).

Example 2

Octenolysis of Different Oils

The oils used in example 2 were subjected to cross-metathesis with a liquid alpha-olefin (i.e., 1-octene) according to the procedure described above. 1-Octene, 99% obtained from Spectrum was distilled, filtered through activated alumina, degassed by sparging with argon for 1 hour/L and stored over activated alumina in a glove box under an argon atmosphere. The ratio of moles of 1-octene per moles of double bond in oil was typically equal to 3 (unless specified otherwise). The results are provided in Table 3.

TABLE 3

Octenolysis of Different Oils

| Entry | Oil | Temp. (° C.) | Time (hr) | Catalyst (Loading) | 9DA GC Area (%) | TON$_{9DA}$ |
|---|---|---|---|---|---|---|
| 1 | MO | 40 | 4 | C848 (20 ppm) | 20.8 | 10,400 |
| 2 | MO | 40 | 4 | C848 (10 ppm) | 18.6 | 18,600 |
| 3 | MO | 40 | 4 | C848 (5 ppm) | 18.9 | 37,800 |
| 4 | MO | 40 | 20 | C848 (5 ppm) | 20.8 | 41,600 |
| 5 | MO | 40 | 4 | C827 (20 ppm) | 20.0 | 10,000 |
| 6 | MO | 40 | 4 | C827 (10 ppm) | 23.0 | 23,000 |
| 7 | MO | 40 | 4 | C827 (5 ppm) | 18.7 | 37,400 |
| 8 | MO | 40 | 20 | C827 (5 ppm) | 20.9 | 41,800 |
| 9 | MO | 40 | 4 | C627 (20 ppm) | 19.3 | 9,650 |
| 10 | MO | 40 | 4 | C627 (10 ppm) | 20.4 | 20,400 |
| 11 | MO | 40 | 4 | C627 (5 ppm) | 16.0 | 32,000 |
| 12 | MO | 40 | 20 | C627 (5 ppm) | 21.3 | 42,600 |
| 13[1] | MO | 40 | 4 | C627 (5 ppm) | 12.7 | 25,400 |
| 14[2] | MO | 40 | 4 | C627 (5 ppm) | 28.5 | 57,000 |
| 15[2] | MO | 40 | 40 | C627 (5 ppm) | 29.5 | 59,000 |
| 16 | MO | 40 | 4 | C712 (5 ppm) | 18.8 | 37,600 |
| 17 | SBO | 40 | 6 | C848 (18 ppm) | 19.0 | 10,555 |
| 18 | SBO | 40 | 6 | C848 (9 ppm) | 19.7 | 21,888 |
| 19 | SBO | 40 | 6 | C827 (18 ppm) | 20.0 | 11,111 |
| 20 | SBO | 40 | 6 | C827 (9 ppm) | 19.5 | 21,666 |
| 21 | SBO | 40 | 6 | C627 (18 ppm) | 19.7 | 10,944 |
| 22 | SBO | 40 | 6 | C627 (9 ppm) | 18.0 | 20,000 |
| 23 | Soy FAME | 40 | 4 | C848 (20 ppm) | 20.0 | 10,000 |
| 24 | Soy FAME | 40 | 4 | C848 (10 ppm) | 15.4 | 15,400 |
| 25 | Soy FAME | 40 | 4 | C827 (20 ppm) | 19.5 | 9,700 |
| 26 | Soy FAME | 40 | 4 | C827 (10 ppm) | 12.9 | 12,900 |
| 27 | Canola FAME | 40 | 4 | C848 (20 ppm) | 21.5 | 10,800 |
| 28 | Canola FAME | 40 | 4 | C848 (10 ppm) | 20.0 | 20,000 |
| 29 | Canola FAME | 40 | 4 | C827 (20 ppm) | 20.5 | 10,300 |
| 30 | Canola FAME | 40 | 4 | C827 (10 ppm) | 20.7 | 21,000 |
| 31 | Canola FAME | 40 | 4 | C627 (20 ppm) | 21.3 | 10,650 |
| 32 | Canola FAME | 40 | 4 | C627 (10 ppm) | 20.0 | 20,000 |
| 33 | Canola FAME | 40 | 4 | C712 (20 ppm) | 20.0 | 10,000 |
| 34 | Canola FAME | 40 | 4 | C712 (10 ppm) | 20.0 | 20,000 |

[1] 1-octene/olefinic substrate double bonds = 1
[2] 1-octene/olefinic substrate double bonds = 10

Example 3

1-Propene Cross-Metathesis Reaction

Soy FAME, (Chemol, IF-24298) was flashed distilled under vacuum (<1 mm Hg). Degassed Soy FAME 7.5 L (6.8 Kg, 22.9 mol) and 0.74 g (25 ppm/double bond) metathesis catalyst 827 were added to a 20 L Pair Reactor under an argon atmosphere. The mixture was degassed with argon for 30 inmates. 1-Propene was added while heating to 60° C., the pressure of the reaction was between 130 psi to 150 psi. The 1-propene was added using a one-way check valve to prevent back flow into the 1-propene cylinder. After 4 hours, GC analysis indicated 9.8% I-decene, 5.4% 2-undecene, 17.5% methyl 9-decenoate and 1.3.9% methyl 2-undecenoate.

The pressure was released and vented into a fume hood. When the reactor was at ambient pressure, 50 ml of 1 M THMP solution in IPA (50 mol equivalents) was added, the reactor degassed with argon and heated to 60° C. overnight (~18 hr).

The reactor was cooled to room temp, ~2.5 L of the reaction mixture was added to 4 L separatory funnel and washed with 1 L of water and 1 L of brine. This was repeated until the Parr reactor was emptied. The combined washed metathesis product was dried over sodium sulfate, filtered and distilled under reduced pressure.

Metathesis products were purified by vacuum distillation using a 2"×36" distillation column packed with 0.16" stainless Pro-Pak™ distillation packing containing a vacuum distillation head. The vacuum was maintained at 2 mmHg.

Table 4 lists the 4 main products from the vacuum distillation of propenoiysis of Soy FAME.

TABLE 4

Products from the Cross Metathesis of 1-Propene and Soy FAME[1]

| Compound | GC Area percent | Isolated Yields (g) |
|---|---|---|
| 1-Decene | 9.8% | 231.0 |
| 2-Undecene | 5.4% | 183.1 |
| Methyl 9-Decenoate | 17.5% | 547.1[2] |
| Methyl 9-Undecenoate | 13.9% | 398.8[3] |

[1]Metathesis Reaction #129-075 and 129-076 and Distillation Results #129-085
[2]Isolated 280.6 g of 98.0% purity and 293.5 g of 79.7% purity
[3]Isolated 170.9 g of 94.2% purity and 227.9 g of 80.5% purity Example 4

Propenolysis of SBO

The soybean oil used in example 1 was subjected to cross-metathesis with 1-propene using C827 according to She procedure described above. The reactions were performed at 60° C. and under 130 psi of 1-propene. The results are provided in Table 5.

TABLE 5

Propenolysis of SBO[1]

| Entry | Catalyst Amt. (ppm) | Time (h) | $1C_{10}$ (%) | $E$-$2C_{11}$ + $Z$-$2C_{11}$ (%) | 9DA (%) | 9UDA (%) | Yield (%) | $TON_{9DA}$ |
|---|---|---|---|---|---|---|---|---|
| 1 | 75 | 2 | 7.14 | 6.13 | 12.72 | 9.49 | 35.74 | 1696 |
| 2 | 75 | 4 | 6.63 | 4.74 | 16.76 | 10.95 | 39.08 | 2234 |
| 3 | 50 | 2 | 7.52 | 5.55 | 15.97 | 10.80 | 39.84 | 3194 |
| 4 | 50 | 4 | 8.99 | 5.38 | 21.61 | 12.30 | 48.29 | 4322 |
| 5 | 25 | 1 | 7.65 | 6.01 | 18.51 | 14.50 | 46.64 | 7403 |
| 6 | 25 | 2 | 7.31 | 6.33 | 18.70 | 16.05 | 48.39 | 7482 |
| 7 | 25 | 3 | 8.71 | 6.58 | 20.69 | 15.56 | 51.54 | 8275 |
| 8 | 25 | 4 | 8.91 | 6.60 | 21.52 | 15.82 | 52.86 | 8609 |
| 9 | 10 | 1 | 2.91 | 2.92 | 4.71 | 4.73 | 15.27 | 4705 |
| 10 | 10 | 2 | 5.68 | 4.77 | 9.50 | 8.35 | 28.30 | 9501 |
| 11 | 10 | 3 | 7.82 | 5.84 | 14.21 | 10.63 | 38.51 | 14214 |
| 12 | 10 | 4 | 7.89 | 5.40 | 15.59 | 10.89 | 39.77 | 15593 |
| 13 | 10 | 6 | 9.53 | 6.42 | 16.42 | 10.74 | 43.11 | 16423 |

[1]Percentages correspond to GC area

Example 5

Propenolysis of Methyl Soyate

Soy FAME was subjected to cross-metathesis with 1-propene using C827 according to the procedure described above. Soy FAME obtained from Chemol was distilled and degassed by sparging with argon for 1 hour/L prior to being stored over activated alumina in a glove box under an argon atmosphere. The reactions were performed at 60° C. and under 130 psi of 1-propene (unless specified otherwise). The results are provided in Table 6.

TABLE 6

Propenolysis of Methyl Soyate[1]

| Entry | Catalyst Amt. (ppm) | Time (h) | $1C_{10}$ (%) | $E$-$2C_{11}$ + $Z$-$2C_{11}$ (%) | 9DA (%) | 9UDA (%) | Yield (%) | $TON_{9DA}$ |
|---|---|---|---|---|---|---|---|---|
| 1[2] | 75 | 4 | 5.60 | 4.79 | 9.69 | 8.15 | 28.23 | 1292 |
| 2 | 75 | 4 | 6.82 | 5.56 | 11.89 | 8.84 | 33.11 | 1585 |
| 3 | 25 | 1 | 10.51 | 7.73 | 22.39 | 15.68 | 56.30 | 8955 |
| 4 | 25 | 2 | 10.78 | 7.51 | 22.51 | 15.10 | 55.90 | 9006 |
| 5 | 25 | 3 | 11.06 | 7.35 | 23.72 | 14.89 | 57.01 | 9486 |
| 6 | 25 | 4 | 11.47 | 7.40 | 23.68 | 14.88 | 57.42 | 9470 |
| 7 | 10 | 0.5 | 8.67 | 6.42 | 16.36 | 11.54 | 42.99 | 16359 |
| 8 | 10 | 1 | 9.78 | 6.40 | 18.90 | 12.13 | 47.21 | 18898 |
| 9 | 10 | 2 | 10.08 | 6.43 | 19.87 | 12.33 | 48.71 | 19871 |

TABLE 6-continued

Propenolysis of Methyl Soyate[1]

| Entry | Catalyst Amt. (ppm) | Time (h) | $1C_{10}$ (%) | $E\text{-}2C_{11} + Z\text{-}2C_{11}$ (%) | 9DA (%) | 9UDA (%) | Yield (%) | $TON_{9DA}$ |
|---|---|---|---|---|---|---|---|---|
| 10 | 10 | 3 | 10.20 | 6.41 | 20.00 | 12.32 | 48.92 | 20001 |
| 11 | 10 | 4 | 10.17 | 6.43 | 20.13 | 12.36 | 49.10 | 20134 |
| 12 | 10 | 6 | 10.12 | 6.45 | 20.35 | 12.39 | 49.31 | 20347 |
| 13 | 5 | 1.5 | 0.76 | 0.92 | 1.01 | 0.53 | 3.22 | 2020 |
| 14 | 5 | 4 | 0.82 | 0.99 | 1.07 | 1.01 | 3.89 | 2140 |
| 15 | 2.5 | 1.5 | 0.18 | 0.23 | 0.22 | 0.21 | 0.84 | 880 |
| 16 | 2.5 | 4 | 0.21 | .027 | 0.27 | 1.01 | 1.76 | 1080 |

[1] Percentages correspond to GC area.
[2] Reaction performed with 100 psi propene.

Example 6

Propenolysis of Fames

Various FAMEs were subjected to cross-metathesis with 1-propene using C827 according to the procedure described above. Canola FAME was the same as in example 1, Soy FAME was the same as in example 4, and Sun FAME was obtained from Nu-Chek-Prep and degassed by sparging with argon for 1 hour/L prior to being stored over activated alumina in a glove box under an argon atmosphere. The reactions were performed at 60° C. and under 130 psi of 1-propene using 5 ppm of catalyst. The results are provided in Table 7.

TABLE 7

Propenolysis of Various FAMEs[1]

| Entry | Seed Oil | Time (h) | $1C_{10}$ (%) | $2C_{11}$ (%) | 9DA (%) | 9UDA (%) | Yield (%) | $TON_{9DA}$ |
|---|---|---|---|---|---|---|---|---|
| 1 | Canola FAME | 2 | 10.53 | 7.59 | 16.75 | 11.39 | 46.26 | 33500 |
| 2 | Canola FAME | 4 | 10.42 | 7.56 | 16.93 | 11.47 | 46.38 | 33860 |
| 3 | Canola FAME | 2 | 10.9 | 7.64 | 16.97 | 11.38 | 46.89 | 33940 |
| 4 | Canola FAME | 4 | 11.09 | 7.85 | 17.82 | 11.85 | 48.61 | 35640 |
| 5 | SBO FAME | 2 | 0.77 | 0.98 | 0.98 | 0.94 | 3.67 | 1960 |
| 6 | SBO FAME | 4 | 0.72 | 0.95 | 0.96 | 0.92 | 3.55 | 1920 |
| 7 | Sun FAME | 2 | 0.51 | 0.61 | 0.56 | 0.61 | 2.29 | 1120 |
| 8 | Sun FAME | 4 | 0.5 | 0.6 | 0.55 | 0.62 | 2.27 | 1100 |
| 9 | Sun FAME | 2 | 3.1 | 3.21 | 3.3 | 3.16 | 12.77 | 6600 |
| 10 | Sun FAME | 4 | 2.79 | 3.02 | 3.21 | 3.14 | 12.16 | 6420 |

[1] Percentages correspond to GC area.

Example 7

Propenolysis of Fames

The FAMEs used in example 5 were subjected to cross-metathesis with 1-propene using C848 and C827 according to the procedure described above. The reactions were performed at 60° C. (unless specified otherwise) and under 130 psi of 1-propane for 4 hours using different catalyst loadings. The results are provided in Table 8.

TABLE 8

Propenolysis of FAMEs[1]

| Entry | Seed Oil | Catalyst (ppm) | $1C_{10}$ (%) | $2C_{11}$ (%) | 9DA (%) | 9UDA (%) | Yield (%) | $TON_{9DA}$ |
|---|---|---|---|---|---|---|---|---|
| 1 | Sun FAME | C827 (28) | 18.65 | 13.65 | 21.32 | 15.16 | 68.78 | 7614 |
| 2 | Canola FAME | C827 (18) | 13.19 | 9.63 | 20.78 | 14.91 | 58.51 | 11544 |
| 3 | Sun FAME | C827 (11) | 15.45 | 10.64 | 23.95 | 14.63 | 64.67 | 21773 |
| 4 | Canola FAME | C827 (7) | 13.41 | 8.69 | 20.72 | 13.48 | 56.3 | 29600 |
| 5[2] | SBO FAME | C848 (25) | 8.67 | 4.38 | 27.52 | 13.39 | 53.96 | 11008 |
| 6[2] | Canola FAME | C848 (18) | 15.19 | 9.65 | 25.74 | 15.68 | 66.26 | 14300 |

[1] Percentages correspond to GC areas.
[2] Reactions performed at 40° C.

Example 8

Cross-Methathesis of Methyl 9-Dodecenoate

Methyl 9-Dodecenoate ($9C_{12}O_2Me$) and 3-Buten-1-yl Acetate were reacted in a cross-metathesis reaction, as described above, using C827 (500 ppm) as die catalyst. Results are presented in Table 9.

TABLE 9

Cross-Metathesis of Methyl 9-Dodecenoate and Buten-1-yl Acetate[1]

| Entry | Time (min) | Temp (° C.) | 3-Buten-1-yl Acetate (%) | $9C_{10}O_2Me$ (%) | $9C_{12}O_2Me$ (%) | $12Ac9C_{12}O_2Me$[2] (%) | $9C_{18}(O_2Me)_2$ (%) |
|---|---|---|---|---|---|---|---|
| 1 | 30 | 60 | 10.8 | 19.9 | 11.2 | 34.5 | 11.8 |
| 2 | 60 | 25 | 11.7 | 18.1 | 10.3 | 34.2 | 11.4 |
| 3 | 120 | 25 | 11.4 | 17.3 | 9.9 | 34.1 | 11.5 |
| 4 | 240 | 25 | 11.4 | 17.4 | 10.0 | 34.4 | 11.6 |
| 5 | 480 | 25 | 11.4 | 17.8 | 10.2 | 34.7 | 11.8 |

[1]Percentages correspond to GC area
[2]$12Ac9C_{12}O_2Me$ is 1-Methyl-12-Acetoxy-9-Dodecenoate Methyl 9-Dodecenoate ($9C_{12}O_2Me$) and 3-buten-1-yl trimethylsilyl ether were reacted in a cross-metathesis reaction, as described above, using C827 (500 ppm) as the catalyst. Results are presented in Table 10.

TABLE 10

Cross-Metathesis of Methyl 9-Dodecenoate and Buten-1-yl Trimethylsilyl Ether[1]

| Entry | Time (min) | Temp (° C.) | $9C_{10}O_2Me$ (%) | $9C_{12}O_2Me$ (%) | $12TMS9C_{12}O_2Me$ (%) |
|---|---|---|---|---|---|
| 1 | 30 | 60 | 19.4 | 41.3 | 19.8 |
| 2 | 60 | 25 | 18.6 | 40.5 | 20.6 |
| 3 | 120 | 25 | 18.2 | 40.5 | 20.9 |
| 4 | 240 | 25 | 17.8 | 40.5 | 25.0 |

[1]Percentages correspond to GC area
[2]$12TMS9C_{12}O_2Me$ is 1-Methyl-12-Trimethylsilyloxy-9-Dodecenoate

Example 9

1-Butene Cross-Metathesis Reaction

Soy FAME, (Chemol, IF-24298) was flashed distilled under vacuum (<1 mm Hg). Degassed Soy FAME 7.5 L (6.8 Kg, 22.9 mol) and 0.74 g (25 ppm/double bond) metathesis catalyst 827 were added to a 20 L Parr Reactor and degassed with argon for 1 hr. 1-Butene was added while heating to 60° C., the pressure of the reaction was between 24 psi to 59 psi. The 1-butene was added using a one-way cheek valve to prevent back flow into the 1-butene cylinder.

After 4 hours, GC analysis indicated 10.5% 1-decene, 8.2% 3-dodecene, 19.6% methyl 9-decenoate and 14.6% methyl 3-dodecenoate. The pressure was released and vented into a fume hood. When the reactor was at ambient pressure, 50 ml of 1 M THMP solution in IPA (50 mol equivalents) was added, the reactor degassed with argon and heated to 60° C. overnight (~18 hr).

The reactor was cooled to room temp and the contents were transferred to a 12 L flask with bottom out drain. The product was washed with 4 L of water and 4 L of brine. The washed metathesis product was dried over sodium sulfate, filtered and distilled under reduced pressure.

Table 11 lists the 4 main products from the vacuum distillation of butenoiysis of Soy FAME.

TABLE 11

Products from the Cross Metathesis of 1-Butene and Soy FAME[1]

| Compound | GC Area Percent | Isolated Yields (g) |
|---|---|---|
| 1-Decene | 10.5% | 458.6 |
| 3-Dodecene | 8.2% | 475.1 |
| Methyl 9-Decenoate | 19.6% | 1494.5[2] |
| Methyl 9-Dodecenoate | 14.6% | 1085.0[3] |

[1]Metathesis reaction #129-061 and distillation results of #108-100
[2]Isolated 846.0 g of 96.9% purity and 648.5 g of 82.6% purity
[3]Isolated 989.8 g of 97.1% purity and 95.2 g o 64.3% purity

Example 10

Butenolysis of Soy Fame

Soy FAME was reacted according to the general metathesis procedure provided above, using the catalysts identified below. 1-Butene was introduced in the reactor while the oil was cooled to 0° C. until about 3 equivalents of 1-butene/double bond of soy FAME were condensed. The reaction vessel was then sealed and the reaction mixture left at the indicated temperature for 4 hours before it was analyzed (the pressure inside the vessel would reach from about 30 psi to about 90 psi). The results are presented in Table 12.

TABLE 12

Butenolysis of Soy FAME using various catalysts

| Entry | Catalyst | Loading (ppm/DB) | Temp. (° C.) | 1-decene (%) | 3-dodecene (%) | $9C_{10}O_2Me$ (%) | $9C_{12}O_2Me$ (%) |
|---|---|---|---|---|---|---|---|
| 1 | C697 | 200 | 60 | 5.31 | 8.09 | 13.31 | 16.3 |
| 2 | C701 | 200 | 60 | 1 | 1.43 | 1.5 | 1.25 |

TABLE 12-continued

Butenolysis of Soy FAME using various catalysts

| Entry | Catalyst | Loading (ppm/DB) | Temp. (° C.) | 1-decene (%) | 3-dodecene (%) | 9C$_{10}$O$_2$Me (%) | 9C$_{12}$O$_2$Me (%) |
|---|---|---|---|---|---|---|---|
| 3 | C712 | 200 | 30 | 5.39 | 7.26 | 18.04 | 19.04 |
| 4 | C801 | 200 | 50 | 0.35 | 0.39 | 0.76 | 0.67 |
| 5 | C933 | 200 | 30 | 6.25 | 7.01 | 15.03 | 13.68 |
| 6 | C838 | 200 | 50 | 0 | 0.002 | 0.013 | 0.002 |
| 7 | C601 | 200 | 50 | 0.11 | 0.14 | 0.16 | 0.1 |
| 8 | C841-n | 200 | 60 | 3.27 | 4.69 | 5.24 | 5.2 |
| 9 | C727 | 200 | 30 | 0.65 | 4.93 | 1.12 | 2.74 |
| 10 | C831 | 200 | 30 | 6.98 | 6.54 | 17.8 | 15.22 |

Example 11

Propenolysis of Soy Fame

Soy FAME was reacted according to the general metathesis procedure provided above, using the catalysts identified in the table, 1-Propene was introduced into the sealed, pre-cooled reactor held at the indicated temperature by a cooling bath. The reaction mixture was stirred at the indicated temperature for up to 40 hours. Samples-were analyzed by GC analysis. The results are presented in Table 13.

TABLE 13

Low Temperature Propenolysis using Various 2nd Generation Grubbs Catalysts

| Exp# | Oil | α-olefin (XS) | Cat (ppm) | Temp (° C.) | Time (h) | % 1C10 | % 2C11 | % 9DA | % 9uDA |
|---|---|---|---|---|---|---|---|---|---|
| 129-072 | SBO FAME | propene | C827 (50) | 20 | 24 | 0 | 0 | 0 | 0 |
| 129-073 | " | " | C827 (50) | 10 | 24 | 0 | 0 | 0 | 0 |
| 129-074 | " | " | C727 (50) | 20 | 24 | 0 | 0 | 0 | 0 |
| 129-075 | " | " | C627 (50) | 20 | 24 | 0 | 0 | 0 | 0 |
| 129-076 | " | " | C727 (50) | 0 | 24 | 0 | 0 | 0 | 0 |
| 129-077 | " | " | C627 (50) | 0 | 24 | 0 | 0 | 0 | 0 |
| 129-080 | " | " | C727 (500) | 20 | 4 | 3.08 | 2.74 | 6.64 | 5.17 |
| 129-081 | " | " | C627 (500) | 20 | 4 | 13.53 | 8.85 | 26.65 | 12.31 |
| 129-082 | " | " | C831 (500) | 20 | 5 | 10.92 | 7 | 20.06 | 12.95 |
| 129-083 | " | " | C727 (500) | 10 | 1.25 | 0.1 | 0.2 | 0.46 | 0.4 |
| 129-084 | " | " | C627 (500) | 10 | 1.25 | 1.08 | 5.38 | 14.48 | 9.97 |
| 129-085 | " | " | C831 (500) | 10 | 40 | 0.65 | 1.2 | 3.93 | 3.22 |
| 129-086 | " | " | C727 (500) | 0 | 3.5 | 0 | 0 | 0 | 0 |
| 129-087 | " | " | C627 (500) | 0 | 3.5 | 0 | 0 | 0 | 0 |
| 129-088 | " | " | C831 (5000) | 0 | 4 | 11.16 | 8.19 | 18.27 | 13.43 |
| 129-089 | " | " | C627 (5000) | 0 | 4 | 10.76 | 7.87 | 19.02 | 13.89 |

Example 12

Treatment of Seed Oils to Remove Impurities

Experiments were conducted to evaluate the effect of impurity removal from various oils prior to use of the oils according to the general metathesis procedure provided above. Treatment procedures were developed using magnesol and sodium bisulfite. The effect of impurity removal from the oil was evaluated by determining the catalyst turnover efficiency (TON) for methyl 9-decenoate (9DA) using various catalysts as indicated in the table below.

The magnesol treatment procedure, generally reduces the peroxide value in the seed oils prior to propenolysis and is summarized as follows: a 3-necked, 500 mL round bottom flask was filled with 300 g of oil (e.g., soy FAME) and the oil stirred under nitrogen sparge conditions. The oil was heated to 80° C. and held at this temperature for 45 minutes to degas, Magnesol (2.5 wt. % or 5 wt. %) was then added along with 1.5 wt. % Celite, with the mixture held for 1 hour or more- to allow adsorption to take place, the contact time being adjusted according to a visual observation of the mixture clarity. Heating was then stopped and the mixture sparged with nitrogen at 4° C. The mixture was next filtered using a Buchner funnel with #4 filter paper and then twice through #2 filter paper. The filtrate was removed for storage in amber glass containers (typically two 125 mL bottles and one 60 mL jar) with a 5 minute nitrogen headspace sparge of the storage containers (1 minute blanket headspace). The containers were capped and sealed for storage. Samples were also obtained for analytical evaluation.

The sodium bisulfite treatment procedure also generally reduces the peroxide value, in the seed oils prior to propenolysis and is summarized as follows: a 3-necked, 500 mL round bottom flask was filled with 300 g of oil (e.g., soy FAME) along with 0.83% sodium bisulfite in 30 g water and the oil mixture stirred under nitrogen sparge conditions. The mixture was heated to 60° C. and held at this temperature for 45 minutes to degas, followed by 90 minutes more time at 60° C. Heating was then stopped and the mixture sparged with nitrogen at 40° C. The mixture was next poured into a separatory funnel with approx. 300 mL warm water and shaken vigorously to wash. Following separation, the bottom water layer was drained. Washing was typically repeated three times. A Rotovap was used to dry the top layer, with a vacuum pulled under nitrogen before heating to 80° C. The lowest vacuum, was maintained for 1-2 hrs, followed by cooling to 30-40° C. and sparging with nitrogen. The separated material was removed for storage in amber glass containers (typically two 125 mL bottles and one 60 mL jar) with a 5 minute nitrogen headspace sparge of the storage containers (1 minute blanket headspace). The containers were capped and sealed for storage. Samples were also obtained for analytical evaluation.

Propenolysis experiments were conducted using treated SBO and Soy FAME with the catalysts identified in the table below. 1-Propene was introduced into a sealed, pre-cooled reactor held at the indicated temperature by a cooling bath, The reaction mixture was stirred for 4 hours at 60° C. The results are presented in Table 14.

TABLE 14

Propenolysis of Treated SBO and Soy FAME

| Exp# | Oil | Lot # | Cat (ppm) | Treatment | 1$C_{10}$ % | 2$C_{11}$ % | 9DA % | 9uDA % | C18:0 | TON$_{9DA}$ | TON$_{total}$ | 9DA/C18:0 |
|---|---|---|---|---|---|---|---|---|---|---|---|---|
| 129-108A | Soy FAME | B6 | C827 (10) | Magnesol[1] | 8.33 | 5.24 | 24.90 | 16.38 | 5.58 | 24900 | 54850 | 4.46 |
| 129-108D | Soy FAME | " | C827 (5) | Magnesol[1] | 8.07 | 4.92 | 24.06 | 13.95 | 5.63 | 48120 | 102000 | 4.27 |
| 129-108E | Soy FAME | " | C827 (2.5) | Magnesol[1] | 6.99 | 4.45 | 20.08 | 11.97 | 5.62 | 80320 | 173960 | 3.57 |
| 129-108F | Soy FAME | " | C827 (1) | Magnesol[1] | 7.47 | 5.10 | 19.22 | 12.10 | 5.21 | 192200 | 438900 | 3.69 |
| 129-108B | Biodiesel | B7 | C827 (10) | Magnesol[2] | 8.27 | 5.28 | 25.17 | 15.65 | 5.44 | 25170 | 54370 | 4.63 |
| 129-108G | " | " | C827 (5) | Magnesol[2] | 8.21 | 5.00 | 23.45 | 13.39 | 5.55 | 46900 | 100100 | 4.23 |
| 129-108H | " | " | C827 (2.5) | Magnesol[2] | 5.52 | 3.95 | 14.68 | 9.31 | 5.49 | 58720 | 133840 | 2.67 |
| 129-108I | " | " | C827 (1) | Magnesol[2] | 2.98 | 2.15 | 5.38 | 4.34 | 5.12 | 53800 | 148500 | 1.05 |
| 129-108C | " | B8 | C827 (10) | Magnesol[1] | 8.14 | 5.23 | 24.48 | 14.96 | 5.58 | 24480 | 52810 | 4.39 |
| 129-108J | " | " | C827 (5) | Magnesol[1] | 7.43 | 4.59 | 20.88 | 11.95 | 5.34 | 41760 | 89700 | 3.91 |
| 129-108K | " | " | C827 (2.5) | Magnesol[1] | 5.04 | 4.33 | 10.64 | 7.49 | 5.07 | 42560 | 110000 | 2.10 |
| 129-108L | " | " | C827 (1) | Magnesol[1] | 4.67 | 4.22 | 9.16 | 6.84 | 5.02 | 91600 | 248900 | 1.82 |
| 129-108M | " | C5 | C827 (10) | $NaHSO_3$ | 7.95 | 5.04 | 24.37 | 14.89 | 5.14 | 24370 | 52250 | 4.74 |
| 129-108N | SBO | D1 | C827 (10) | Magnesol[2] | 7.89 | 4.83 | 24.25 | 14.25 | 5.15 | 24250 | 51220 | 4.71 |
| 129-108O | " | D4 | C827 (10) | Magnesol[2] | 7.15 | 5.55 | 20.15 | 15.67 | 5.31 | 20150 | 48520 | 3.79 |

[1]Added 2.5 wt % Magnesol
[2]Added 5.0 wt % Magnesol

Example 13

Butenolysis and Propenolysis of Soy Fame and Other Oils

Additional experiments were conducted with Soy FAME and other oils according to fee general metathesis procedure provided above, using the catalysts identified below. 1-Butene or 1-propene was introduced in the reactor while the oil was cooled to 0° C. until about 3 equivalents of α-olefin/double bond of soy FAME or other oil were condensed. The reaction vessel was then sealed and the reaction mixture left at the indicated temperature for the time period indicated below (ranging from 2-5 hours) before it was analyzed (the pressure inside the vessel would range from about 50-70 psi for the butenolysis reaction and up to about 130 psi for the propenolysis reaction). The results are presented in Table 15.

TABLE 15

Butenolysis and Propenolysis of Soy FAME or Other Oil using various catalysts

| Entry | Oil | Catalyst ID | Loading (ppm) | α-olefin | Temp. (° C.) | Pressure (psi) | Time (hr) | 9DA GC (Area %) | $TON_{9DA}$ |
|---|---|---|---|---|---|---|---|---|---|
| GM-94-100B | Soy FAME | DPA1-278 | 50 | butene | 60 | 70 | 4 | 19.8 | 3960 |
| GM-94-100A | Soy FAME | C524 | 50 | butene | 60 | 70 | 4 | 4.9 | 980 |
| GM-94-99A | Soy FAME | C552 | 50 | butene | 60 | 70 | 4 | 4.2 | 840 |
| GM-94-99B | Soy FAME | C566 | 50 | butene | 60 | 70 | 4 | 4.5 | 900 |
| JP-176-044 | Soy FAME | C571 | 100 | butene | 60 | 70 | 4 | 27.1 | 2710 |
| AF-178-023 | Soy FAME | C578 | 100 | butene | 60 | 70 | 2 | 7.1 | 706 |
| AF-178-040 | Soy FAME | C578 | 500 | butene | 60 | 70 | 4 | 11.7 | 234 |
| GM-94-098A | Soy FAME | C598 | 100 | butene | 60 | 70 | 4 | 26.5 | 2650 |
| AF-178-025 | Soy FAME | C598cs | 100 | butene | 60 | 70 | 2 | 20.7 | 2074 |
| JP-176-034 | Soy FAME | C601 | 100 | butene | 60 | 70 | 4 | 7.5 | 750 |
| AF-178-035 | Soy FAME | C606 | 100 | butene | 60 | 70 | 4 | 11.6 | 1160 |
| JP-176-035 | Soy FAME | C613 | 100 | butene | 60 | 70 | 4 | 31.9 | 3190 |
| GM-94-98B | Soy FAME | C626 | 100 | butene | 60 | 70 | 4 | 30.6 | 3060 |
| AF-178-032 | Soy FAME | C629 | 100 | butene | 60 | 70 | 4 | 20.2 | 2020 |
| AF-178-037 | Soy FAME | C657 | 100 | butene | 60 | 70 | 4 | 24.2 | 2420 |
| JP-176-036 | Soy FAME | C672 | 100 | butene | 60 | 70 | 4 | 31.0 | 3100 |
| AF-178-009 | Soy FAME | C702 | 2.5 | butene | 60 | 70 | 3 | 11.8 | 47200 |
| JP-125-174 | Soy FAME | C712 | 200 | butene | 60 | 70 | 4 | 18.0 | 900 |
| AF-178-024 | Soy FAME | C727 | 100 | butene | 60 | 70 | 4 | 26.4 | 2640 |
| AF-178-034 | Soy FAME | C734 | 100 | butene | 60 | 70 | 4 | 29.9 | 2990 |
| AF-178-031 | Soy FAME | C767 | 100 | butene | 60 | 70 | 3 | 14.1 | 1410 |
| AF-178-020 | Soy FAME | C782 | 100 | butene | 60 | 70 | 2 | 15.7 | 1570 |
| AF-178-036 | Soy FAME | C782 | 100 | butene | 60 | 70 | 4 | 13.6 | 1360 |
| AF-178-030 | Soy FAME | C793 | 100 | butene | 60 | 70 | 4 | 22.1 | 2210 |
| AF-178-021 | Soy FAME | C809 | 100 | butene | 60 | 70 | 2 | 22.1 | 2210 |
| JP-176-037 | Soy FAME | C823 | 100 | butene | 60 | 70 | 4 | 8.5 | 850 |
| AF-178-026 | Soy FAME | C831 | 100 | butene | 60 | 70 | 3 | 21.7 | 2170 |
| AF-178-038 | Soy FAME | C833 | 500 | butene | 60 | 70 | 4 | 11.6 | 1160 |
| AF-178-027 | Soy FAME | C833 | 100 | butene | 60 | 70 | 3 | 7.0 | 700 |
| GM-94-101A | Soy FAME | C833 | 100 | butene | 40 | 50 | 4 | 1.2 | 120 |
| AF-178-033 | Soy FAME | C849 | 100 | butene | 60 | 70 | 4 | 32.4 | 3240 |
| AF-178-014 | Soy FAME | C859 | 2.5 | butene | 60 | 70 | 4 | 14.5 | 58085 |
| GM-94-101B | Soy FAME | C859 | 100 | butene | 40 | 50 | 4 | 22.8 | 2280 |
| JP-176-045 | Soy FAME | C866 | 100 | butene | 60 | 70 | 4 | 8.3 | 830 |
| AF-178-022 | Soy FAME | C884 | 100 | butene | 60 | 70 | 4 | 26.1 | 2610 |
| AF-178-029 | Soy FAME | C923 | 100 | butene | 60 | 70 | 3 | 8.8 | 880 |
| AF-178-039 | Soy FAME | C923 | 500 | butene | 60 | 70 | 4 | 16.7 | 1670 |
| AF-178-018 | Soy FAME | C933 | 100 | butene | 60 | 70 | 2 | 20.3 | 2030 |
| AF-178-028 | Soy FAME | C949 | 100 | butene | 60 | 70 | 3 | 17.3 | 1730 |
| AM-093-141F | Sunflower FAME | C827 | 25 | propene | 60 | 100 | 3 | 18.1 | 7240 |
| TU-164-158 | Sunflower oil | C627 | 50 | butene | 60 | 70 | 4 | 7.2 | 1440 |
| GM-94-103B | Sunflower oil | C827 | 50 | butene | 60 | 70 | 4 | 19.3 | 3860 |
| GM-94-103A | Sunflower FAME | C627 | 50 | butene | 60 | 70 | 4 | 21.1 | 4220 |
| AM-129-180 | Methyl linoleate | C827 | 25 | butene | 60 | 70 | 4 | 24.4 | 9760 |
| TU-164-157 | Methyl linoleate | C627 | 50 | butene | 60 | 70 | 4 | 19.6 | 3920 |
| TU-164-153 | Methyl oleate | C627 | 50 | butene | 60 | 70 | 5 | 18.7 | 3740 |
|  | Oleic acid | C827 | — | butene |  |  |  |  |  |
|  | Oleic acid | C627 | — | butene |  |  |  |  |  |
|  | Olive oil | C827 | — | butene |  |  |  |  |  |
| AF-178-046 | Olive oil | C627 | 50 | butene | 60 | 70 | 4 | 3.0 | 600 |
|  | Castor oil | C827 | — | butene |  |  |  |  |  |
| AF-178-042 | Castor oil | C627 | 50 | butene | 60 | 70 | 4 | 3.2 | 640 |
|  | Peanut oil | C827 | — | butene |  |  |  |  |  |

TABLE 15-continued

Butenolysis and Propenolysis of Soy FAME or Other Oil using various catalysts

| Entry | Oil | Catalyst ID | Loading (ppm) | α-olefin | Temp. (° C.) | Pressure (psi) | Time (hr) | 9DA GC (Area %) | $TON_{9DA}$ |
|---|---|---|---|---|---|---|---|---|---|
| AF-178-044 | Peanut oil | C627 | 50 | butene | 60 | 70 | 4 | 0.5 | 100 |
| TU-164-155 | Canola FAME | C627 | 35 | butene | 60 | 70 | 5 | 25.6 | 7314 |
| TU-164-156 | Palm FAME | C627 | 63 | butene | 60 | 70 | 5 | 17.6 | 2794 |
| AM-129-006 | Palm FAME | C827 | 10 | propene | 60 | 130 | 4 | 17.4 | 17400 |

Example 14

Comparison of Ethenolysis and Alkenolysis Results

The foregoing ethenolysis and alkenolysis results are summarized in Table 16.

TABLE 16

Comparison of Ethenolysis and Alkenolysis Results

| Entry | Substrate | Olefin | Pressure (psi) | Temp (° C.) | Time (hours) | Catalyst | Loading (ppm) | 9DA GC Area % | $TON_{9DA}$ |
|---|---|---|---|---|---|---|---|---|---|
| 1 | MO | Ethylene | 150 | 40 | 4 | C827 | 10 | 0.6 | 600 |
| 2 | | Ethylene | 150 | 40 | 2 | C827 | 100 | 24.2 | 2,400 |
| 3 | | 1-Octene | — | 40 | 4 | C827 | 10 | 23.0 | 23,000 |
| 4 | SBO | Ethylene | 150 | 40 | 6 | C827 | 10 | 0.3 | 300 |
| 5 | | Propene | 130 | 60 | 6 | C827 | 10 | 16.4 | 16,423 |
| 6 | | 1-Octene | — | 40 | 6 | C827 | 18 | 20.0 | 11,111 |
| 7 | SBO | Ethylene | 150 | 40 | 6 | C627 | 22 | 6.4 | 2,910 |
| 8 | | 1-Octene | — | 40 | 6 | C627 | 18 | 19.7 | 10,944 |
| 9 | Soy | Ethylene | 150 | 40 | 4 | C827 | 10 | 1.2 | 1,200 |
| 10 | FAME | Propene | 130 | 60 | 6 | C827 | 10 | 20.4 | 20,347 |
| 11 | | 1-Octene | — | 40 | 4 | C827 | 10 | 12.9 | 12,900 |
| 12 | Soy | Ethylene | 150 | 40 | 4 | C823 | 67 | 13.3 | 1,985 |
| 13 | FAME | 1-Butene | 70 | 60 | 4 | C823 | 100 | 8.5 | 850 |
| 14 | | 1-Butene | 70 | 60 | 4 | C601 | 100 | 7.5 | 750 |
| 15 | | 1-Butene | 70 | 60 | 3 | C833 | 100 | 7.0 | 700 |
| 16 | | 1-Butene | 70 | 60 | 3 | C923 | 100 | 8.8 | 880 |
| 17 | Canola | Ethylene | 150 | 40 | 4 | C827 | 10 | 0.4 | 400 |
| 18 | FAME | Propene | 130 | 60 | 4 | C827 | 25 | 16.9 | 33,860 |
| 19 | | 1-Octene | — | 40 | 4 | C827 | 10 | 20.7 | 21,000 |
| 20 | Canola | Ethylene | 150 | 40 | 4 | C712 | 10 | 2.6 | 2,600 |
| 21 | FAME | 1-Octene | — | 40 | 4 | C712 | 10 | 20.0 | 20,000 |

As may be noted, alkenolysis provided significantly increased turnover results for 9DA for certain catalysts, such as C827 (an N-heterocyclic carbene containing catalyst), as compared with ethenolysis results using the same catalysts.

The invention claimed is:

1. A method for synthesizing a terminal olefin, the method comprising: contacting, in the presence of a metathesis catalyst, an olefinic substrate comprising a mixture of internal olefins with a cross metathesis partner comprised of an alpha olefinic reactant, under reaction conditions effective to allow cross-metathesis to occur, wherein the reaction conditions include a reaction temperature of at least 35° C., and wherein the internal olefins are selected from the group consisting of: monoglycerides, diglycerides, triglycerides, and combinations thereof.

2. The method of claim 1, wherein the reaction conditions effective to ensure that the olefinic substrate and the cross-metathesis partner are in liquid form.

3. The method of claim 1, wherein the olefinic substrate is an oil or a compound derived from an oil.

4. The method of claim 1, wherein the olefinic substrate is a fatty acid ester.

5. A method for synthesizing a terminal olefin, the method comprising: contacting, in the presence of a metathesis catalyst, an olefinic substrate comprised of at least one internal olefin with a cross metathesis partner comprised of an alpha olefinic reactant, under reaction conditions effective to allow cross-metathesis to occur, wherein the reaction conditions include a reaction temperature of at least 35° C., wherein the olefinic substrate is a seed oil or a compound derived from a seed oil.

6. The method of claim 5, wherein the olefinic substrate is selected from the group consisting of: canola oil, soybean oil, sunflower oil, safflower oil, cottonseed oil, castor oil, rapeseed oil, peanut oil, corn oil, olive oil, palm oil, sesame oil, grapeseed oil, fatty acid esters thereof, and combinations thereof.

7. The method of claim 1, wherein the alpha olefinic reactant is selected from the group consisting of: mono-substituted olefins, di-substituted olefins, and combinations thereof.

8. The method of claim 7, wherein the alpha olefinic reactant contains one or two substituents each having 1 to about 10 carbon atoms.

9. The method of claim 8, wherein the alpha olefinic reactant is a mono-substituted olefin having 1 to about 10 carbon atoms.

10. The method of claim 9, wherein the alpha olefinic reactant is selected from the group consisting of: 1-propene, 1-butene, 1-pentene, 1-hexene, 1-heptene, 1-octene, 1-nonene, 1-decene and combinations thereof.

11. The method of claim 1, wherein the alpha olefinic reactant has a solubility of at least 0.25 M in the olefinic substrate.

12. The method of claim 1, wherein the contacting is carried out in an atmosphere and/or solution selected from the group consisting of: an oxygen containing atmosphere, an inert atmosphere, or an oxygen free atmosphere and solution.

13. A method for synthesizing a terminal olefin, the method comprising: contacting, in the presence of a metathesis catalyst, an olefinic substrate comprised of at least one internal olefin with a cross metathesis partner comprised of an alpha olefinic reactant, under reaction conditions effective to allow cross-metathesis to occur, wherein the reaction conditions include a reaction temperature of at least 35° C., wherein the method provides a terminal olefin having a turnover number of at least twice the turnover number obtained for an identical reaction in which ethylene is substituted for the alpha olefinic reactant.

14. The method of claim 13, wherein the turnover number at least five times the turnover number obtained for an identical reaction in which ethylene is substituted for the alpha olefinic reactant.

15. The method of claim 1, wherein the metathesis catalyst is a ruthenium alkylidene metathesis catalyst which has the structure of formula (II):

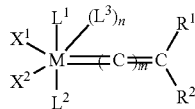
(II)

wherein:
M is ruthenium;
n is 0 or 1;
m is 0, 1, or 2;
$L^1$, $L^2$ and $L^3$ are neutral electron donor ligands;
$X^1$ and $X^2$ are anionic ligands;
$R^1$ and $R^2$ are independently selected from hydrogen, hydrocarbyl, substituted hydrocarbyl, heteroatom-containing hydrocarbyl, substituted heteroatom-containing hydrocarbyl, and functional groups;
wherein any two or more of $X^1$, $X^2$, $L^1$, $L^2$, $L^3$, $R^1$, and $R^2$ can be taken together to form a cyclic group, and further wherein any one of $X^1$, $X^2$, $L^1$, $L^2$, $L^3$, $R^1$, and $R^2$ can be attached to a support.

16. The method of claim 15, wherein n and m are 0; $R^1$ is hydrogen, and $R^2$ is selected from $C_1$-$C_{20}$ alkyl, $C_2$-$C_{20}$ alkenyl, and aryl, optionally substituted with one or more moieties selected from $C_1$-$C_6$ alkyl, $C_1$-$C_6$ alkoxy and phenyl; $L^2$ is selected from phosphine, sulfonated phosphine, phosphite, phosphinite, phosphonite, arsine, stibine, ether, amine, amide, imine, sulfoxide, carboxyl, nitrosyl, pylidine, substituted pylidine, imidazole, substituted imidazole, pyrazine, and thioether; and $X^1$ and $X^2$ are independently selected from hydrogen, halide, $C_1$-$C_{20}$ alkyl, $C_5$-$C_{20}$ aryl, $C_1$-$C_{20}$ alkoxy, $C_5$-$C_{20}$ aryloxy, $C_2$-$C_{20}$ alkoxycarbonyl, $C_6$-$C_{20}$ aryloxycarbonyl, $C_2$-$C_{20}$ acyl, $C_2$-$C_{20}$ acyloxy, $C_1$-$C_{20}$ alkylsulfonato, $C_5$-$C_{20}$ arylsulfonato, $C_1$-$C_{20}$ alkylsulfanyl, $C_5$-$C_{20}$ arylsulfanyl, $C_1$-$C_{20}$ alkylsulfinyl, or $C_5$-$C_{20}$ arylsulfinyl, any of which, with the exception of hydrogen and halide, are optionally further substituted with one or more groups selected from halide, $C_1$-$C_6$ alkyl, $C_1$-$C_6$ alkoxy, and phenyl.

17. The method of claim 15, wherein $L^1$ has the structure of formula (III)

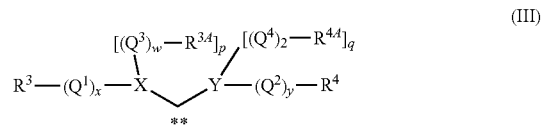
(III)

in which:
X and Y are heteroatoms selected from N, O, S, and P;
p is zero when X is O or S, and p is 1 when X is N or P;
q is zero when Y is O or S, and q is 1 when Y is N or P;
$Q^1$, $Q^2$, $Q^3$, and $Q^4$ are independently selected from hydrocarbylene, substituted hydrocarbylene, heteroatom-containing hydrocarbylene, substituted heteroatom-containing hydrocarbylene, and —(CO)—, and further wherein two or more substituents on adjacent atoms within Q may be linked to form an additional cyclic group;
w, x, y, and z are independently zero or 1; and
$R^3$, $R^{3A}$, $R^4$, and $R^{4A}$ are independently selected from hydrogen, hydrocarbyl, substituted hydrocarbyl, heteroatom-containing hydrocarbyl, and substituted heteroatomcontaining hydrocarbyl,
such that the transition metal complex is a ruthenium carbene complex having the structure of formula (IV)

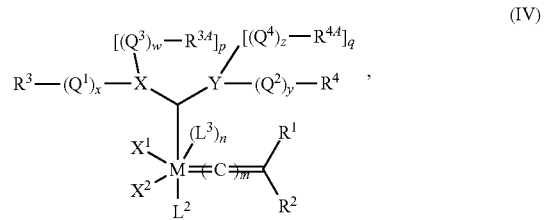
(IV)

wherein any two or more of $X^1$, $X^2$, $L^2$, $L^3$, $R^1$, $R^2$, $R^3$, $R^{3A}$, $R^4$, an $R^{4A}$ can be taken together to form a cyclic group, and further wherein any one of $X^1$, $X^2$, $L^2$, $L^3$, $R^1$, $R^2$, $R^3$, $R^{3A}$, $R^4$, and $R^{4A}$ can be attached to a support.

18. A method for synthesizing a terminal olefin, the method comprising: contacting, in the presence of a metathesis catalyst, an olefinic substrate comprised of at least one internal olefin with a cross metathesis partner comprised of an alpha olefinic reactant, under reaction conditions effective to allow cross-metathesis to occur, wherein the reaction conditions include a reaction temperature of at least 35° C., wherein the metathesis catalyst is a ruthenium alkylidene metathesis catalyst that has the structure of formula (VI)

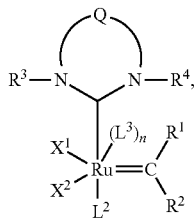

(VI)

wherein:

n is 0 or 1;

$L^2$ and $L^3$ are neutral electron donor ligands;

$X^1$ and $X^2$ are anionic ligands;

$R^1$ and $R^2$ are independently selected from hydrogen, hydrocarbyl, substituted hydrocarbyl, heteroatom-containing hydrocarbyl, substituted heteroatom-containing hydrocarbyl, and functional groups;

$R^3$ and $R^4$ are independently selected from hydrogen, hydrocarbyl, substituted hydrocarbyl, heteroatom-containing hydrocarbyl, and substituted heteroatom-containing hydrocarbyl, wherein any two or more of $X^1$, $X^2$, $L^2$, $L^3$, $R^1$, and $R^2$ can be taken together to form a cyclic group, and further wherein any one of $X^1$, $X^2$, $L^2$, $L^3$, $R^1$, and $R^2$ can be attached to a support; and wherein Q is a hydrocarbylene, substituted hydrocarbylene, heteroatom-containing hydrocarbylene, or substituted heteroatom-containing hydrocarbylene linker, and further wherein two or more substituents on adjacent atoms within Q may be linked to form an additional cyclic group.

19. The method of claim 18, wherein Q has the structure —$CR^{11}R^{12}$—$CR^{13}R^{14}$— or —$CR^{11}$=$CR^{13}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups, and or wherein any two of $R^{11}$, $R^{12}$, $R^{13}$, and $R^{14}$ may be linked together to form a substituted or unsubstituted, saturated or unsaturated ring.

20. The method of claim 19, wherein $R^1$ is hydrogen, and $R^2$ is selected from $C_1$-$C_{20}$ alkyl, $C_2$-$C_{20}$ alkenyl, and aryl, optionally substituted with one or more moieties selected from $C_1$-$C_6$ alkyl, $C_1$-$C_6$ alkoxy and phenyl, $L^2$ is selected from phosphine, sulfonated phosphine, phosphite, phosphinite, phosphonite, arsine, stibine, ether, amine, amide, imine, sulfoxide, carboxyl, nitrosyl, pylidine, substituted pylidine, imidazole, substituted imidazole, pyrazine, and thioether; $X^1$ and $X^2$ are independently selected from hydrogen, halide, $C_1$-$C_{20}$ alkyl, $C_5$-$C_{20}$ aryl, $C_1$-$C_{20}$ alkoxy, $C_5$-$C_{20}$ aryloxy, $C_2$-$C_{20}$ alkoxycarbonyl, $C_6$-$C_{20}$ aryloxycarbonyl, $C_2$-$C_{20}$ acyl, $C_2$-$C_{20}$ acyloxy, $C_1$-$C_{20}$ alkylsulfonato, $C_5$-$C_{20}$ arylsulfonato, $C_1$-$C_{20}$ alkylsulfanyl, $C_5$-$C_{20}$ arylsulfanyl, $C_1$-$C_{20}$ alkylsulfinyl, or $C_5$-$C_{20}$ arylsulfinyl, any of which, with the exception of hydrogen and halide, are optionally further substituted with one or more groups selected from halide, $C_1$-$C_6$ alkyl, $C_1$-$C_6$ alkoxy, and phenyl; $R^3$ and $R^4$ are aromatic, substituted aromatic, heteroaromatic, substituted heteroaromatic, alicyclic, substituted alicyclic, heteroatom-containing alicyclic, or substituted heteroatom-containing alicyclic, composed of from one to about five lings; and $R^{12}$ and $R^{14}$ are hydrogen, and $R^{11}$ and $R^{13}$ are selected from hydrogen, lower alkyl and phenyl, or are linked to form a cyclic group.

21. A method for synthesizing a terminal olefin, the method comprising: providing an olefinic substrate having at least one internal olefin; providing an alpha olefin having at least 3 carbon atoms; and contacting the olefinic substrate with the alpha olefin in the presence of less than approximately 1000 ppm of a metathesis catalyst relative to the number of olefinic substrate double bonds, under reaction conditions effective to allow cross-metathesis to occur; wherein the contacting yields a product having at least 0.2 wt% 9DA, and the catalyst has a $TON_{9DA}$ of approximately 100 or greater.

22. The method of claim 21, wherein the contacting occurs in the presence of approximately 100 ppm or less of the catalyst.

23. The method of claim 21, wherein the contacting occurs in the presence of approximately 50 ppm or less of the catalyst.

24. The method of claim 21, wherein the contacting occurs in the presence of approximately 10 ppm or less of the catalyst.

25. The method of claim 21, wherein the contacting yields a product having at least about 5 wt % 9DA.

26. The method of claim 21, wherein the $TON_{9DA}$ is approximately 1000 or greater.

* * * * *

UNITED STATES PATENT AND TRADEMARK OFFICE
CERTIFICATE OF CORRECTION

PATENT NO.         : 8,569,560 B2                                     Page 1 of 1
APPLICATION NO.    : 13/622613
DATED              : October 29, 2013
INVENTOR(S)        : Yann Schrodi et al.

It is certified that error appears in the above-identified patent and that said Letters Patent is hereby corrected as shown below:

In the Claims

In column 53, claim 1, line 61, before "diglycerides, triglycerides, and" replace "monoqlycerides," with --monoglycerides,--.

In column 55, claim 14, about line 25, before "at least five times the turnover" insert --is--.

In column 56, claim 17, lines 38-39, after "and substituted" replace "heteroatomcontaining" with --heteroatom-containing--.

Signed and Sealed this
Twelfth Day of August, 2014

Michelle K. Lee
*Deputy Director of the United States Patent and Trademark Office*